(12) United States Patent
Feng et al.

(10) Patent No.: US 10,596,268 B2
(45) Date of Patent: Mar. 24, 2020

(54) CONJUGATE OF DEZOCINE AND POLYETHYLENE GLYCOL

(71) Applicant: JenKem Technology Co., Ltd. (Beijing), Beijing (CN)

(72) Inventors: Zewang Feng, Beijing (CN); Jinliang Wang, Beijing (CN); Yanli Xiong, Beijing (CN); Xuan Zhao, Beijing (CN)

(73) Assignee: JENKEM TECHNOLOGY CO., LTD. (BEIJING), Beijing (CN)

( * ) Notice: Subject to any disclaimer, the term of this patent is extended or adjusted under 35 U.S.C. 154(b) by 0 days.

(21) Appl. No.: 16/446,872

(22) Filed: Jun. 20, 2019

(65) Prior Publication Data
US 2019/0298845 A1    Oct. 3, 2019

Related U.S. Application Data

(63) Continuation of application No. PCT/CN2017/116157, filed on Dec. 14, 2017.

(30) Foreign Application Priority Data

Dec. 22, 2016    (CN) .......................... 2016 1 1199383

(51) Int. Cl.
| | | |
|---|---|---|
| *A61K 47/60* | (2017.01) | |
| *A61K 31/135* | (2006.01) | |
| *A61P 25/04* | (2006.01) | |
| *C07C 215/64* | (2006.01) | |
| *A61K 47/55* | (2017.01) | |
| *A61K 47/56* | (2017.01) | |

(52) U.S. Cl.
CPC ............ *A61K 47/60* (2017.08); *A61K 31/135* (2013.01); *A61P 25/04* (2018.01); *C07C 215/64* (2013.01); *Y02P 20/55* (2015.11)

(58) Field of Classification Search
CPC ...... A61K 47/60; A61K 31/135; A61K 47/56; A61K 47/55; C07C 215/64; A61P 25/04; Y02P 20/55
See application file for complete search history.

(56) References Cited

FOREIGN PATENT DOCUMENTS

CN    101646464 A  *  2/2010  ............. A61K 47/60

OTHER PUBLICATIONS

CN-101646464-A (2010) WIPO English Machine Translation; p. 1-80.*

* cited by examiner

*Primary Examiner* — John M Mauro
(74) *Attorney, Agent, or Firm* — Flener IP & Business Law; Zareefa B. Flener

(57) ABSTRACT

The present invention relates to the technical field of medicine, in particular to a conjugate of dezocine and polyethylene glycol and a pharmaceutical composition thereof. The conjugate of dezocine and water-soluble oligomer provided by the present invention has better pharmacokinetic properties and a high drug absorption degree, may reduce the side effects of the drug, and achieve a smaller administration dosage and a more diverse mode of administration, such as oral administration, in clinic. Compared with dezocine, the conjugate of the present invention has a stronger analgesic effect and a longer analgesic duration, may reduce the frequency of drug administration, improve patient compliance, and has advantages in effectiveness and safety of the drug, as well as drug tolerance, etc.

20 Claims, No Drawings

CONJUGATE OF DEZOCINE AND POLYETHYLENE GLYCOL

CROSS-REFERENCE TO RELATED APPLICATION

This application is a continuation application of International patent application No. PCT/CN2017/116157, filed on Dec. 14, 2017, which claims the benefit and priority of Chinese patent application No. CN201611199383.5, filed on Dec. 22, 2016, each of which is incorporated herein by reference in its entirety and for all purposes.

FIELD OF THE INVENTION

The present invention relates to the technical field of medicine, in particular to a conjugate of dezocine and polyethylene glycol, especially a conjugate of dezocine and polyethylene glycol having less side effects and a pharmaceutical composition thereof.

BACKGROUND OF THE INVENTION

Pain is a symptom of many diseases, which makes patients feel pain and may further cause physiological dysfunction. Some long-term severe pain is an unbearable torment to the body. More than one-third of the world's population is suffering from persistent or recurrent pain. The treatment of pain is mainly based on drug therapy. Common analgesics may be classified as follows: non steroidal anti-inflammatory drugs (NSAIDs), opioid analgesics, non-opioid central analgesics, spasmolytic analgesics, and the like, wherein opioid analgesics mainly act on opioid receptors. Opioid receptors are mainly divided into three categories: μ receptors, κ receptors, and δ receptors, each of which has different subtypes. An opioid receptor agonist refers to an agonist mainly acting on μ receptors, such as morphine, which exerts an analgesic effect by stimulating the μ receptors and mimicking an endogenous opioid peptide. A partial agonist of an opioid receptor is an agonist for some receptor subtypes and an antagonist for others, also known as a mixed agonist-antagonist of opioid receptor, such as pentazocine, butorphanol, dezocine, etc. An opioid receptor antagonist has competitive antagonism for various opioid receptors, and has antagonistic strengths followed by μ>κ>δ receptors, such as naloxone, which has a chemical structure similar to that of morphine, except that the N-methyl group of morphine is substituted with an allyl group and the 6-hydroxyl group is changed to a keto group, while its pharmacological action is completely opposite to that of morphine.

From a clinical point of view, an ideal analgesic drug should have the following characteristics: 1) a potent analgesic effect; 2) a noninvasive and convenient way of administration, and quick-acting; 3) a long interval between medications; 4) a low peak-to-valley ratio and a stable plasma concentration; 5) a complete metabolism and non-toxic metabolites; and 6) less adverse reactions and mild degree of adverse reactions.

Dezocine, chemical name: 13-amino-5,6,7,8,9,10,11,12-octahydro-5-methyl-5,11-methylenebenzocyclodecen-3-ol, CAS: 53648-55-8, has the following structural formula:

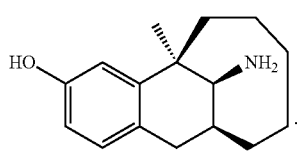 [SMILES: C[C@@]12CCCCC[C@@H](Cc3ccc(O)cc31)[C@@H]2N]

Dezocine is a potent opioid analgesic, which is an opioid receptor-mixed agonist-antagonist fully agonistic to κ receptors and only having a weaker effect on μ receptors. When the blood concentration of dezocine reaches 5-9 μg/L, it produces a potent analgesic effect, which is 5-9 times that of pethidine and equivalent to that of morphine (Strain E C, Preston K L, Liebson I A. Opioid antagonist effects of dezocine in opioid-dependent humans. Clin Pharmacol Ther, 1996, 60(2): 206-217). Studies have shown that the spinal cord κ receptor is an important target for the analgesic effect of dezocine. Dezocine is absorbed quickly and distributed rapidly and has a long half-life in the body, thus has quick onset of analgesia and long-lasting analgesia, and analgesic intensity, onset time and duration comparable to those of morphine, but is less addictive, and is mainly used in the treatment of patients with moderate to severe postoperative pain and chronic pain, viscera angina and cancer pain and other patients with poor analgesic effect or severe side effects in clinical practice.

It is found that adverse reactions occur when the average peak concentration of dezocine reaches 45 μg/L. Common adverse reactions of dezocine include somnolence, nausea, emesis, etc., and adverse reactions such as dizziness, anorexia, disorientation, hallucinations, sweating, tachycardia, and skin reactions at the injection site have also been reported. In addition, dezocine has slight respiratory and circulatory inhibition, which limits the use of dezocine in patients with reduced respiratory reserve, so it needs to be used in hospitals in order to detect respiratory depression in time and conduct appropriate treatment, which virtually reduces the compliance of patients. In terms of addiction, dezocine may cause dysphoria, sedation and mental dependence damage as well as miosis in a dose-dependent manner (Zhou Panke, Lan Zhixun. Research progress on the application of dezocine in postoperative analgesia. Practical Journal of Clinical Medicine, 2011, 8(6): 169-172). At present, only dezocine in injection form has been listed at home and abroad, which limits its application to some extent.

Polyethylene glycol (PEG) modification is a technology for linking activated PEG to a drug molecule or surface, which a novel drug delivery technique developed rapidly in recent years. Patent application CN201080037610.9 discloses conjugates of oxycodone, morphine and codeine covalently linked to polyethylene glycol. The conjugates were subjected to pharmacokinetic analysis by intravenous injection or oral administration of equal doses in rats. Wherein, compared with oxycodone, intravenous administration of PEGylated oxycodone having different oligomeric PEG-lengths ($PEG_1$-$PEG_9$) resulted in variable plasma concentrations and exposures, wherein PEGylated oxycodone having PEG chain lengths of 3, 5, 7 and 9 showed a higher average exposure, PEGylated oxycodone of $PEG_6$ showed a comparable average exposure, and PEGylated oxycodone having a EPG chain length of 1, 2 or 4 showed a slightly lower average exposure. Oral administration of PEGylated oxycodone having different oligomeric PEG-lengths ($PEG_1$-$PEG_9$) resulted in an increase in plasma exposure, with the exception of oxycodone covalently linked to $PEG_1$ and $PEG_3$. The oxycodone covalently linked to $mPEG_6$ had the highest oral bioavailability, followed by $mPEG_5$-oxycodone and $mPEG_7$-oxycodone. Compared with morphine, administration of PEGylated morphine having different PEG-lengths ($PEG_1$-$PEG_9$) resulted in a higher plasma concentrations and exposure; and oral administration of PEG-morphine conjugates resulted in a decrease in oral bioavailability. Among the morphine conjugates with different PEG lengths, PEG$_4$-morphine conjugate showed the greatest bioavailability. Compared with codeine, PEGylated codeine having different oligomeric PEG-lengths (PEG$_1$-PEG$_9$) has only a slight increase in plasma exposure, and the bioavailability of the orally administered PEG-codeine conjugates increased as the PEG-length increased from 2, and the codeine conjugate with PEG$_6$ had the greatest bioavailability. It can be seen that although the above drugs are all opioid receptor agonists, PEGylated drugs may have different effects for different drugs, and the PEGylated drugs with different PEG lengths may have different effects for the same drug. In the above patent application, each terminal group of polyethylene glycol molecule only binds to one drug molecule, which results in an excessively low drug molecule loading rate, and causes a large pressure on pharmaceutical preparation.

SUMMARY OF THE INVENTION

In order to improve the pharmacokinetic properties of dezocine, reduce its adverse reactions, achieve a smaller administration dosage and a more diverse mode of administration, such as oral administration, in clinic, the present invention links dezocine to polyethylene glycol to provide a conjugate as shown in general formula I:

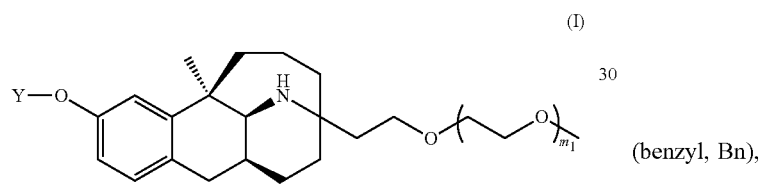

(I)

wherein, Y is selected from: H or a protecting group; and m$_1$ is an integer of 0-20.

Preferably, Y is H.

Preferably, the protecting group is selected from the group consisting of: —CH$_3$ (methyl, Me), —CH$_2$—CH=CH$_2$ (allyl),

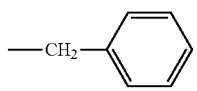

(trimethylsilyl, TMS),

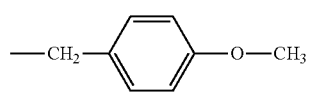

(triethylsilyl, TES),

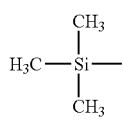

(tert-butyldimethylsilyl, TBS),

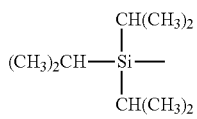

(triisopropylsilyl, TIPS),

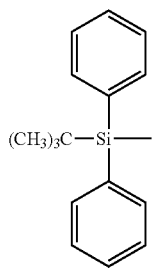 [SMILES: CC(C)(C)[Si](C)(c1ccccc1)c1ccccc1]

(tert-butyldiphenylsilyl, TBDPS),

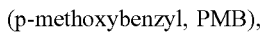

(benzyl, Bn),

(p-methoxybenzyl, PMB),

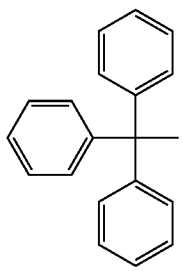 [SMILES: CC(c1ccccc1)(c1ccccc1)c1ccccc1]

(triphenylmethyl, Trt),

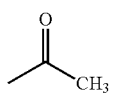

(acetyl, Ac),

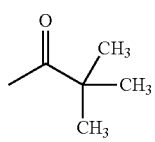

(pivaloyl, Pv),

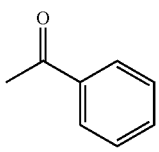

(benzoyl, Bz),

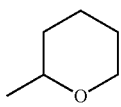

(2-tetrahydropyran, THP),

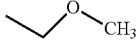

(methoxymethyl, MOM),

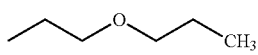

(2-ethoxyethyl, EE), and

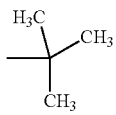

(tert-butyl, t-Bu); more preferably, the protecting group is selected from the group consisting of: —CH$_3$, —CH$_2$—CH═CH$_2$,

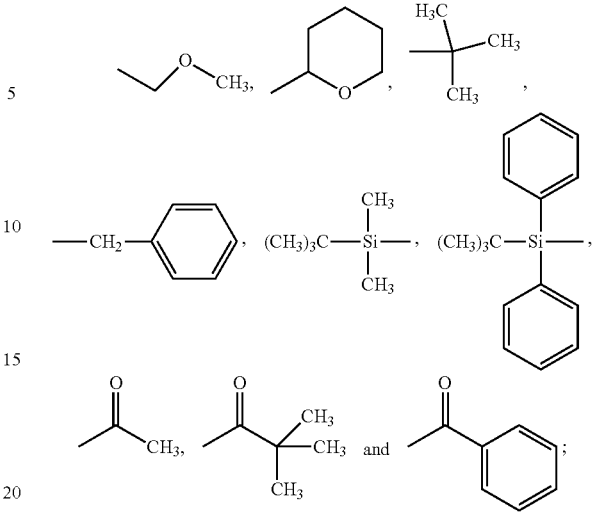

and most preferably, the protecting group is —CH$_3$.

Preferably, $m_1$ is an integer of 1-10, more preferably an integer of 2-8, further preferably an integer of 4-6, and most preferably, $m_1$ is 5.

In a preferred embodiment, the conjugate as shown in general formula I has the following structure:

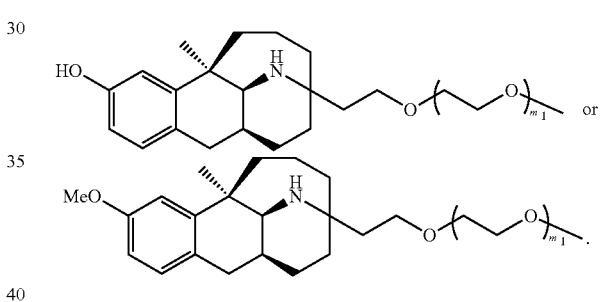

In a more preferred embodiment, the conjugate as shown in general formula I has the following structure:

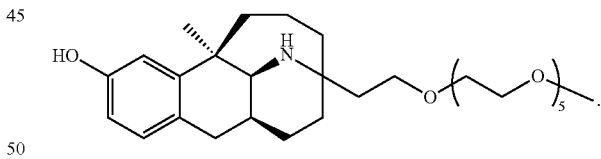

In another aspect, the present invention provides a conjugate of dezocine and polyethylene glycol as shown in general formula II:

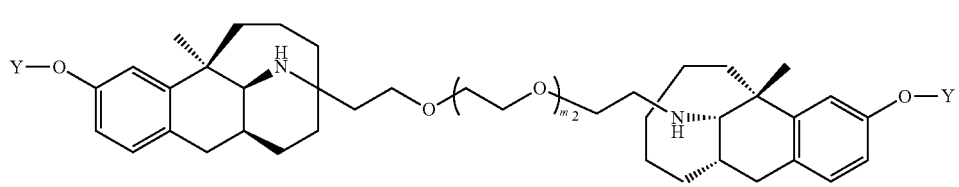

(II)

wherein, Y is selected from: H or a protecting group; and $m_2$ is an integer of 0-20.

Preferably, Y is H.

Preferably, the protecting group is selected from the group consisting of: —CH$_3$, —CH$_2$—CH=CH$_2$, TMS, TES, TBS, TIPS, TBDPS, Bn, PMB, Trt, Ac, Pv, Bz, THP, MOM, EE, and t-Bu; more preferably, the protecting group is selected from the group consisting of: —CH$_3$, —CH$_2$—CH=CH$_2$, TBS, TBDPS, Bn, Bz, Ac, Pv, THP, MOM, and t-Bu; and most preferably, the protecting group is —CH$_3$.

Preferably, $m_2$ is an integer of 1-10, more preferably an integer of 2-8, further preferably an integer of 2-5, and most preferably, $m_2$ is 3.

In a preferred embodiment, the conjugate as shown in general formula II has the following structure:

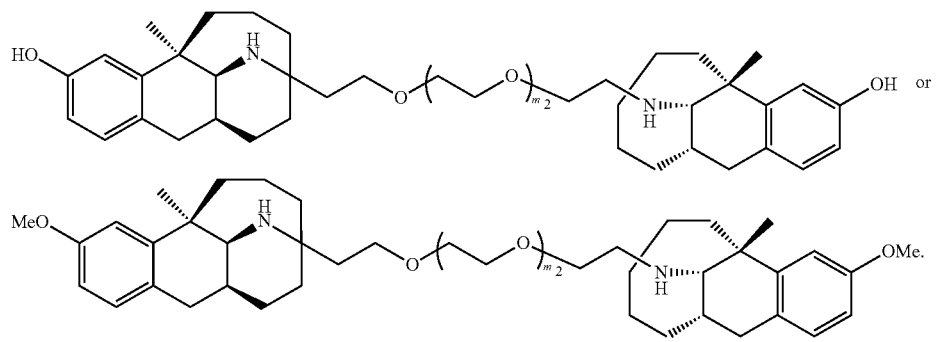

In a more preferred embodiment, the conjugate as shown in general formula II has the following structure:

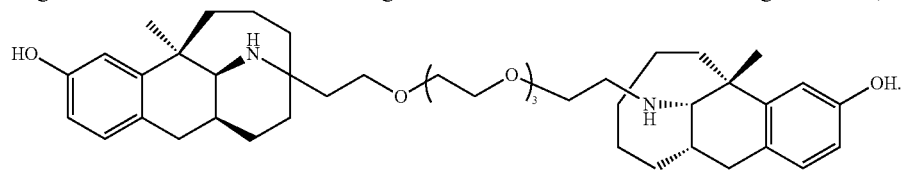

In yet another aspect, the present invention provides a conjugate of dezocine and polyethylene glycol as shown in general formula III:

Wherein, Y is selected from: H or a protecting group; and $m_3$, $m_4$, and $m_5$ are independently selected from an integer of 0-20.

Preferably, Y is H.

Preferably, the protecting group is selected from the group consisting of: —CH$_3$, —CH$_2$—CH=CH$_2$, TMS, TES, TBS, TIPS, TBDPS, Bn, PMB, Trt, Ac, Pv, Bz, THP, MOM, EE, and t-Bu; more preferably, the protecting group is selected from the group consisting of: —CH$_3$, —CH$_2$—CH=CH$_2$, TBS, TBDPS, Bn, Bz, Ac, Pv, THP, MOM, and t-Bu; and most preferably, the protecting group is —CH$_3$.

Preferably, $m_3$, $m_4$, and $m_5$ are independently selected from an integer of 0-15, further preferably an integer of 0-10, more preferably an integer of 1-6; yet further preferably an integer of 2-5, and most preferably, $m_3$, $m_4$, and $m_5$ are 2.

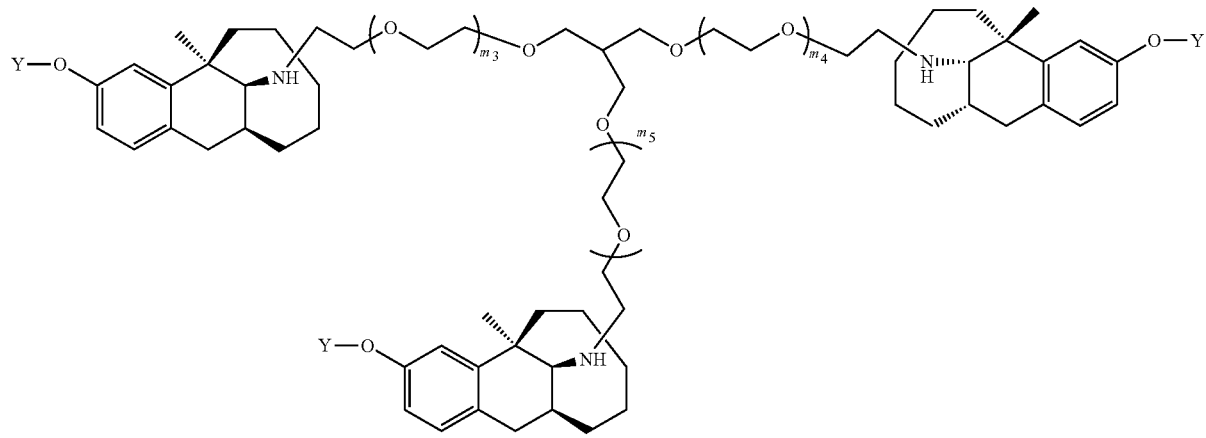

In a preferred embodiment, the conjugate as shown in general formula III has the following structure:
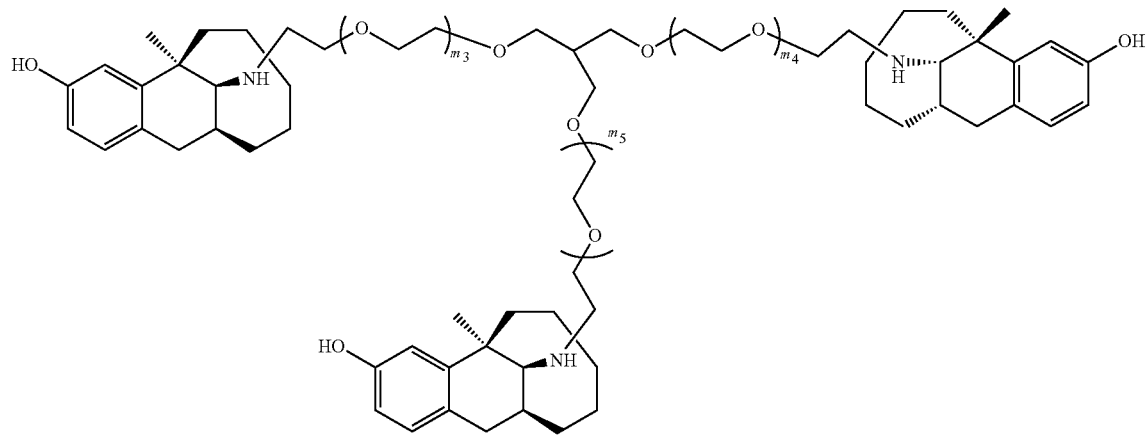
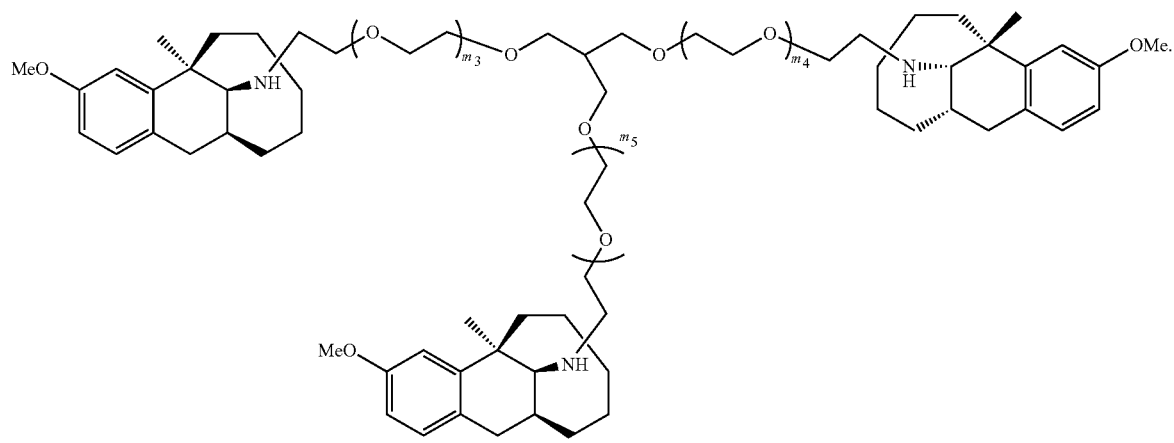
In a more preferred embodiment, the conjugate as shown in general formula III has the following structure:
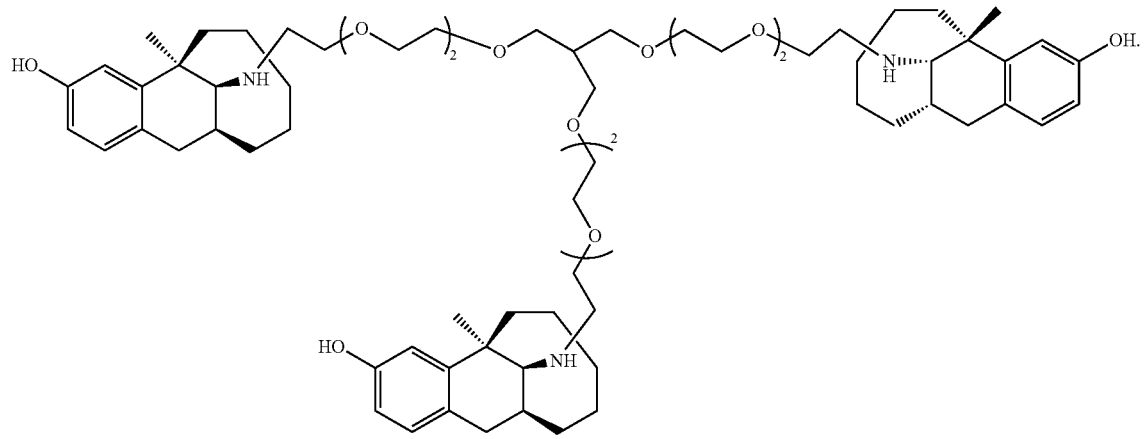
In yet another aspect, the present invention provides a conjugate of dezocine and polyethylene glycol as shown in general formula IV:

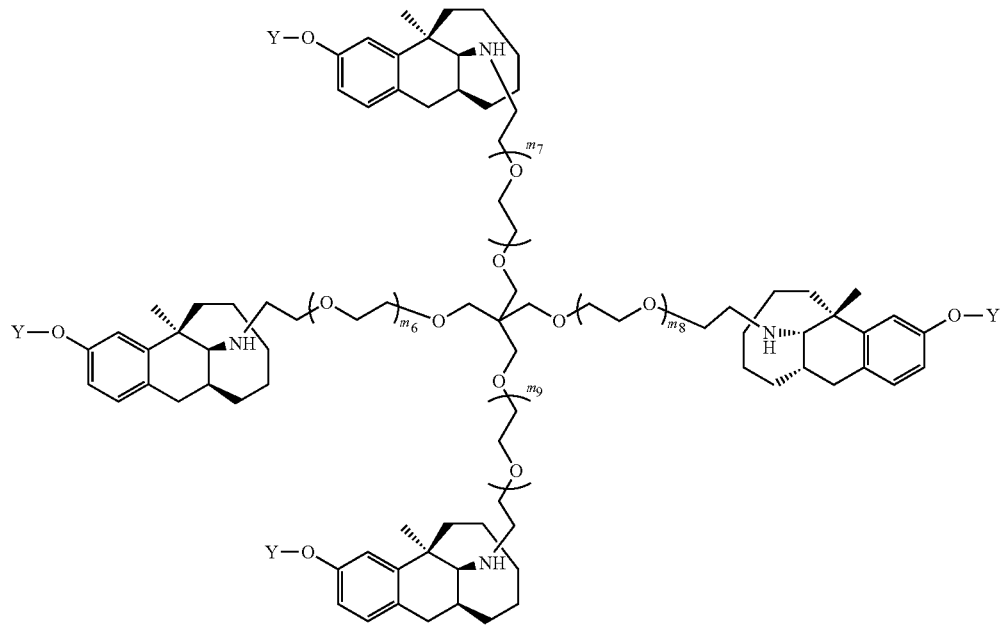

(IV)

Wherein, Y is selected from: H or a protecting group; and $m_6$, $m_7$, $m_8$, and $m_9$ are independently selected from an integer of 0-20.

Preferably, Y is H.

Preferably, the protecting group is selected from the group consisting of: —CH$_3$, —CH$_2$—CH=CH$_2$, TMS, TES, TBS, TIPS, TBDPS, Bn, PMB, Trt, Ac, Pv, Bz, THP, MOM, EE, and t-Bu; more preferably, the protecting group is selected from the group consisting of: —CH$_3$, —CH$_2$—CH=CH$_2$, TBS, TBDPS, Bn, Bz, Ac, Pv, THP, MOM, and t-Bu; and most preferably, the protecting group is —CH$_3$.

Preferably, $m_6$, $m_7$, $m_8$, and $m_9$ are independently selected from an integer of 0-15, further preferably an integer of 0-10, more preferably an integer of 0-6; yet further preferably an integer of 1-5, and most preferably, $m_6$, $m_7$, $m_8$, and $m_9$ are 1.

In a preferred embodiment, the conjugate is

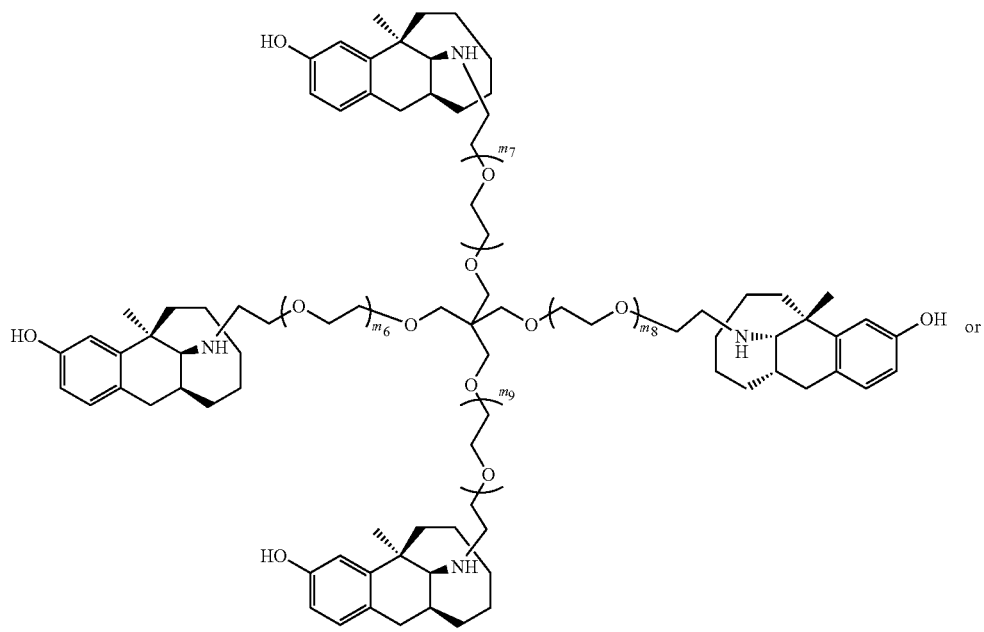

or

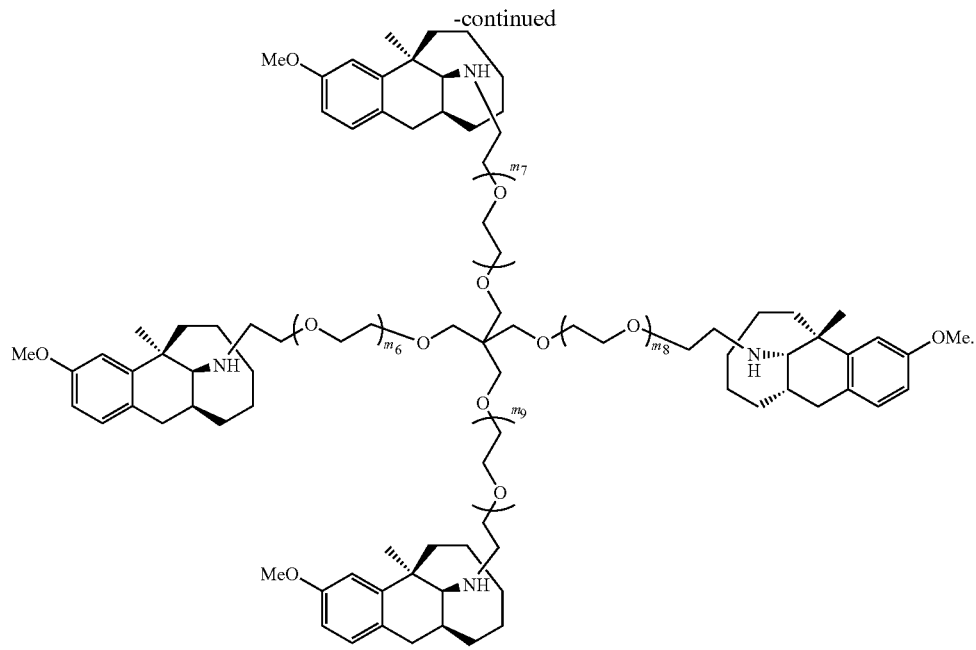

In a more preferred embodiment, the conjugate is

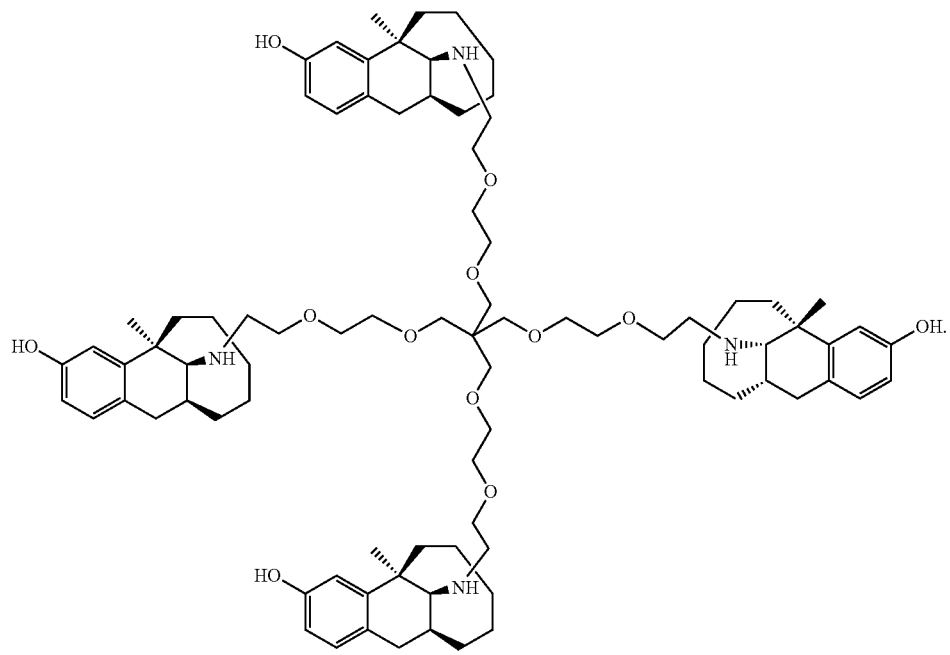

In another aspect, the present invention provides a preparation method of the above conjugate of dezocine and polyethylene glycol, including the following specific steps: modifying a terminal group of polyethylene glycol with a leaving group, and then subjecting the polyethylene glycol to a nucleophilic substitution reaction with dezocine or an intermediate or a derivative thereof to obtain the conjugate of dezocine and polyethylene glycol.

The leaving group is selected from the group consisting of

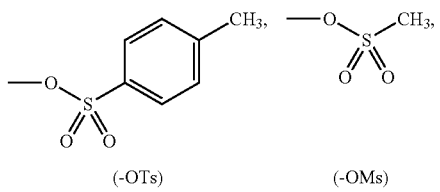

-continued

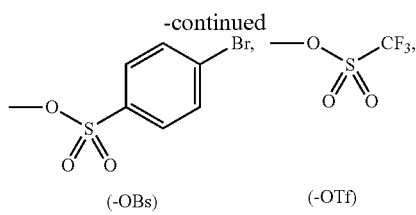

(-OBs) (-OTf)

—F, —I, —Br, and —Cl.

The polyethylene glycol may be linear, Y-shaped or multi-branched, that is, it may be selected from the group consisting of:

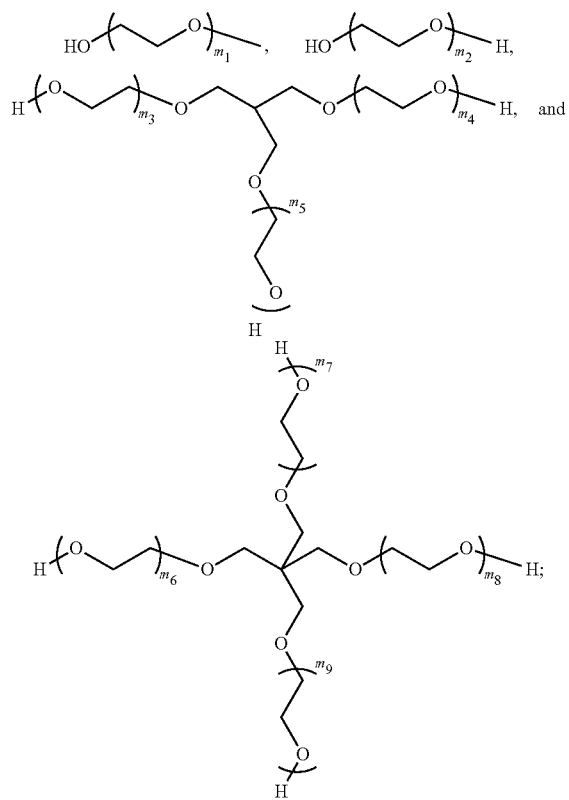

wherein, $m_{1-9}$ are independently selected from an integer of from 1 to 19.

Preferably, the nucleophilic substitution reaction is performed in a polar aprotic solvent at a reaction temperature of −20° C. to 100° C.

Preferably, the polar aprotic solvent is selected from the group consisting of N,N-dimethylformamide (DMF), N,N-diethylformamide, dimethyl sulfoxide (DMSO), hexamethylphosphoramide (HMP), N-methylpyrrolidone (NMP), tetrahydrofuran, acetone, dioxane, acetonitrile, dichloromethane, and chloroform; more preferably, the polar aprotic solvent is selected from the group consisting of N,N-dimethylformamide, N,N-diethylformamide, dimethyl sulfoxide, and tetrahydrofuran; and most preferably, the polar aprotic solvent is tetrahydrofuran.

Preferably, the reaction temperature is preferably −20° C. to 80° C.; more preferably, the reaction temperature is 0° C. to 50° C.; and most preferably, the reaction temperature is room temperature.

Preferably, the nucleophilic substitution reaction is performed under an alkaline condition, and more preferably, the alkaline condition is that with NaH.

Preferably, the L is selected from the group consisting of —OTs, —OMs, —Br and —Cl, and more preferably, the L is —OTs or —OMs.

Preferably, the above preparation method further includes a step of deprotecting: dissolving the conjugate of dezocine and polyethylene glycol, adding a deprotecting reagent, reacting, and then separating and purifying the product.

The deprotecting reagent includes an acidic reagent and an alkaline reagent, and preferably is an acidic reagent.

In an example of the present invention, the deprotecting reagent is boron tribromide.

In another aspect, the present invention provides a pharmaceutical composition comprising the above conjugate and a pharmaceutically acceptable carrier or excipient.

Preferably, the pharmaceutical composition is a tablet, a capsule, a pill, a granule, a powder, a suppository, an injection, a solution, a suspension, a plaster, a patch, a lotion, a drop, a liniment, a spray and other dosage forms.

In another aspect, the present invention provides use of the above conjugate and pharmaceutical composition thereof in the preparation of a medicament.

Preferably, the medicament is an analgesic.

The conjugate provided by the present invention has better pharmacokinetic properties and a high drug absorption degree, may reduce the side effects of the drug, and achieve a smaller administration dosage and a more diverse mode of administration, such as oral administration, in clinic. Compared with dezocine, the conjugate of the present invention has a stronger analgesic effect and a longer analgesic duration, may reduce the frequency of drug administration, improve patient compliance, and has advantages in effectiveness and safety of the drug, as well as drug tolerance, etc.

DETAILED DESCRIPTION OF THE INVENTION

The technical scheme in the embodiments of the present invention will be clearly and completely described below, and it is obvious that the embodiments described are only part of the embodiments of the present invention, not all of them. All other embodiments obtained by those skilled in the art based on the embodiments of the present invention without creative efforts are within the scope of the present invention.

In the present invention, the following terms are used in accordance with the definitions described below:

"Water-soluble" in "water-soluble oligomer" means that at least 35% (by weight, the same hereinafter), preferably 95% or more, of the oligomer is soluble in water at room temperature. Preferably at least 35%, more preferably at least 50%, further preferably at least 70%, still more preferably at least 85%, and most preferably at least 95% or all, of the water soluble polymer is soluble in water. "Oligomer" means a polymer having from 1 to 30 monomers, the structure of which may vary, and the specific oligomers used in the present invention include those having various geometric shapes (e.g., linear type, Y-type, multi-branched type, etc.).

"PEG" or "polyethylene glycol" encompasses all water-soluble poly(ethylene oxide), and unless otherwise stated, all repeating units of "PEG" or "polyethylene glycol" are —$CH_2$—$CH_2$—O— and may contain different capping groups or functional groups. Typically, the PEG used in the present invention includes the following two structures: "—(CH$_2$CH$_2$O)$_m$—" or "—(CH$_2$CH$_2$O)$_{m-1}$—CH$_2$CH$_2$—" depending on whether the terminal oxygen is substituted.

"Capping group" generally refers to a non-reactive group that binds to the terminal oxygen of PEG. For the purposes of the present invention, preferred capping group has a relatively low molecular weight, such as methyl or ethyl. The capping group may also comprise detectable markers including, but not limited to, fluorescers, chemiluminescent agents, enzyme markers, colorimetric markers (such as dyes), metal ions, and radioactive components.

A "protecting group" is a moiety that prevents or stops a specific functional group having chemical reactivity in a molecule from reacting under certain reaction conditions. The protecting groups may vary depending on the protected chemical reactive group and the reaction conditions to be employed, as well as the presence or absence of other reactive or protecting groups in the molecule. The functional groups that may be protected include carboxylic acid group, amino group, hydroxyl group, thiol group, carbonyl group, and the like. The protection of hydroxyl group is mainly to convert it into corresponding ether, ester, etc., and it is more common to convert it into corresponding ether. The ether generally used for the protection of hydroxyl group is mainly silyl ether, methyl ether, allyl ether, benzyl ether, alkoxymethyl ether, alkoxy-substituted methyl ether, etc., and these protecting groups are well known to those skilled in the art.

The conjugate of the present invention may be administered in the form of a pure compound or a suitable pharmaceutical composition, in any acceptable mode of administration or as an agent for similar use. Therefore, administration may be done by oral, intranasal, rectal, transdermal or injection, in the form of a solid, semi-solid, lyophilized powder or liquid medicament, for example, a tablet, a suppository, a pill, a soft and hard gelatin capsules, a powder, a solution, a suspension or aerosol, etc., preferably in unit dosage form suitable for simple administration of precise dosages. The pharmaceutical composition of the present invention may comprise a conventional pharmaceutically acceptable carrier or excipient and the conjugate(s) of the present invention as an active ingredient, and further comprises other medicaments, carriers, adjuvants and the like.

Generally, the pharmaceutically acceptable composition may comprise from 1 to about 99% by weight of the conjugate of the present invention, and from 99 to 1% by weight of a suitable pharmaceutical excipient, depending on the mode of administration desired. Preferably, the composition comprises from about 5 to 75% by weight of the conjugate of the present invention, the balance being a suitable pharmaceutical excipient.

The conjugate or pharmaceutical composition of the present invention may also be formulated in a liquid form for administration, for example, about 0.5 to about 50% of the active ingredient and the optionally present pharmaceutical adjuvant are dissolved or dispersed in a carrier to form a solution or suspension. Examples of the carrier are water, saline, aqueous glucose, glycerol, ethanol, and the like.

If desired, the pharmaceutical composition of the present invention may further comprise minor amounts of auxiliary substances such as wetting or emulsifying agents, pH buffering agents, antioxidants and the like, for example: citric acid, sorbitan monolaurate, triethanolamine oleate, butylated hydroxytoluene, and the like.

The following examples are intended to illustrate the invention but are not intended to limit the invention.

Dezocine and its intermediates VII and X used in the examples were prepared by referring to the paper (Xu Guolian. Process optimization of the Dezocine API intermediates synthesis technology. Nanjing: Nanjing University of Science and Technology, 2012: 6-42), and the synthetic route is as follows. Polyethylene glycol raw materials are provided by Beijing Jenkem Technology Co., Ltd., and other reagents are commercially available.

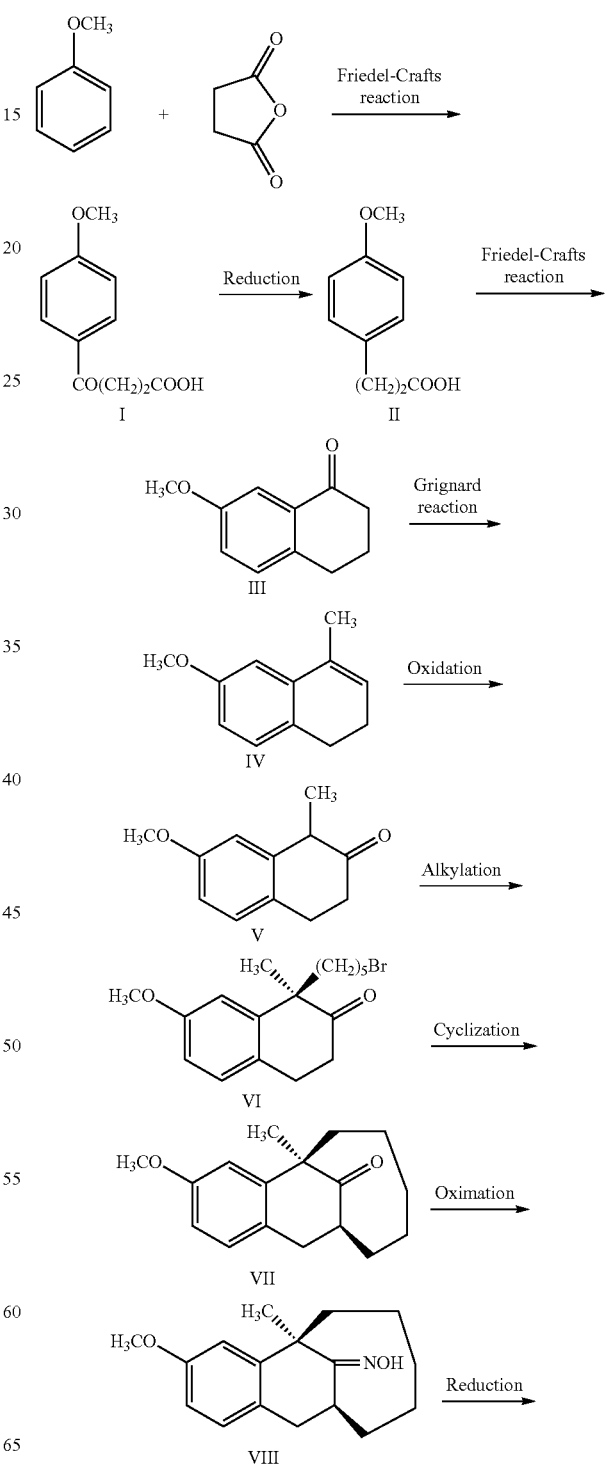

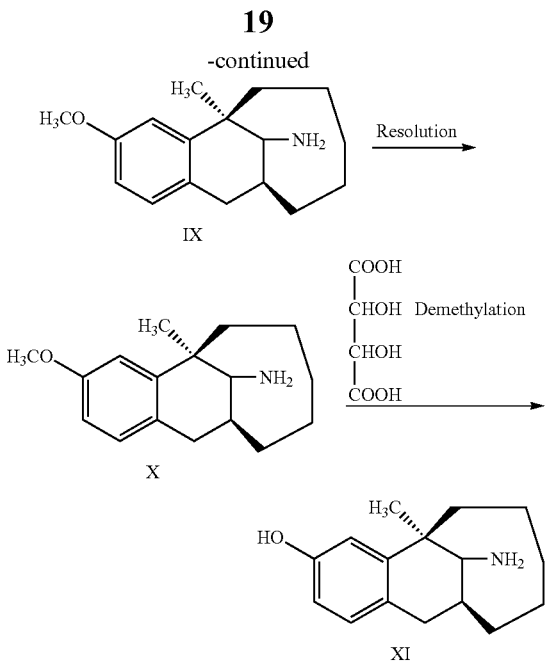

Example 1 Preparation of Monomethoxyhexaethylene Glycol-Dezocine Conjugate (JK-2215D01)

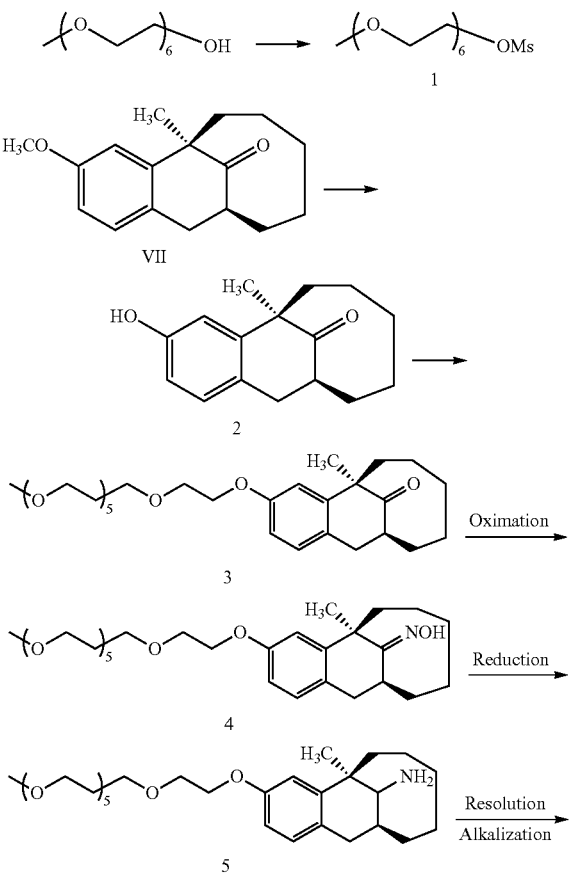

To a reaction flask, hexaethylene glycol monomethyl ether (10.0 g, 131.6 mmol) and dichloromethane (100 mL) were added, and the resulting mixture was stirred and cooled to 0° C. Triethylamine (26.6 g, 263.2 mmol) was added dropwise thereto. The reaction mixture was stirred for 10 minutes. Methanesulfonyl chloride (22.6 g, 197.4 mmol) was added to the reaction mixture. The reaction was carried out with stirring at room temperature. After the reaction was completed, the reaction mixture was added with distilled water, and then extracted with dichloromethane (100 mL×3). The organic layers were combined, washed with distilled water (100 mL×3), dried over anhydrous sodium sulfate, filtered, and concentrated to dryness under reduced pressure to give an oily substance (1) (17.3 g, yield: 86.7%). $^1$H NMR (400 MHz, CDCl$_3$): δ 3.83 (t, 2H), 3.56 (m, 22H), 3.40 (s, 3H), 3.18 (s, 3H).

Compound VII (5.2 g, 20.0 mmol) was dissolved in dichloromethane (100 mL), and cooled to −20° C. under a nitrogen atmosphere. Then, a solution of boron tribromide in dichloromethane (1.0 M, 60 mL) was added dropwise thereto. After the completion of the dropwise addition, the system naturally rose to room temperature and allowed to react overnight. Water (100 mL) was added thereto. The mixture was stirred for 1 h, and then subjected to liquid separation. The water layer was added with aqueous ammonia, and extracted with diethyl ether (100 mL×3). The extracts were combined, washed with saturated brine, dried, filtered and then concentrated. The crude product was purified by column chromatography to give a product (2) (3.7 g, yield: 76%). $^1$H NMR (400 MHz, CDCl$_3$): δ6.86 (d, 1H), 6.77 (s, 1H), 6.51 (d, 1H), 2.86 (d, 2H), 2.73 (m, 1H), 1.92 (t, 2H), 1.55 (m, 5H), 1.31 (in, 6H).

To a reaction flask, intermediate (2) (5.0 g, 19.3 mmol) was added, dissolved in tetrahydrofuran (100 mL), and cooled in an ice bath under a nitrogen atmosphere. Sodium hydride (1.2 g, 29.0 mmol) was added thereto. The resulting mixture was reacted for 30 min. Then, a solution of monomethoxyhexaethylene glycol mesylate (8.7 g, 23.2 mmol) in tetrahydrofuran (50 mL) was added dropwise. After the completion of the dropwise addition, the ice bath was removed. The mixture was continued to react at room temperature. After the reaction was completed, the mixture was concentrated to dryness. The residue was added with water (200 mL), washed with dilute hydrochloric acid and saturated brine, dried, filtered and then concentrated. The crude product was purified by column chromatography to give a product (3) (7.7 g, yield: 74.6%). $^1$H NMR (400 MHz, CDCl$_3$): δ 6.85 (d, 1H), 6.77 (s, 1H), 6.51 (d, 1H), 3.96 (d, 2H), 3.55 (m, 22H), 3.40 (d, 2H), 3.35 (s, 3H), 2.82 (d, 2H), 2.75 (m, 1H), 1.83 (t, 2H), 1.45 (s, 3H), 1.52 (m, 2H), 1.29 (m, 8H).

To a reaction flask, Compound (3) (7.2 g, 20 mmol), hydroxylamine hydrochloride (7 g, 100 mmol) and pyridine (60 mL) were added, and the mixture was heated to 40 to 50° C. and reacted for 5 h, and then reacted under reflux overnight. The reaction mixture was concentrated under reduced pressure to recover pyridine until no liquid was dropped to give a viscous solid. Water and ethyl acetate were added to the viscous solid, and the resulting mixture was stirred, and allowed to stand for stratification. The organic phase was further concentrated. The residue was cooled to room temperature, then allowed to stand overnight, suction filtered, washed with cold ethyl acetate, drained and dried to a white crude product. The crude product was hot-dissolved with 20 times isopropanol, added with activated carbon, refluxed for 1 h, filtered while hot, cooled, crystallized, and suction filtered. The solid was washed with cold isopropanol, drained and dried to give a product (4) (5.7 g, yield: 76%).

Sodium hydroxide (55 g) was dissolved in water, and aluminum-nickel alloy (10 g) was added thereto in batches with stirring. After the addition, the mixture was stirred for 10 min, stirred in a boiling water bath for 30 min, and filtered. The filter cake was washed with water and then with 95% ethanol. The resulting solid was added into a high pressure reactor. Compound (4) (5.2 g, 13.9 mmol), 95% ethanol (20 mL) and aqueous ammonia (5 mL) were added into the high pressure reactor. The mixture was reacted at 40 to 50° C. for 20 h under pressure. The reaction mixture was cooled, and then filtered. The filtrate was evaporated to dryness. The resulting solid was added to 95% ethanol, and concentrated hydrochloric acid was added dropwise. The mixture was refluxed under heating for 30 min, cooled to room temperature and then cooled in an ice-water bath. The precipitated solid was filtered and dried to give a hydrochloride salt of Compound (5) (4.1 g).

The hydrochloride salt of Compound (5) was converted into an alkali with aqueous ammonia, dissolved in methanol, and added to a methanol solution of L-(+)-tartaric acid to obtain a crude product. The crude product was recrystallized from methanol to give a white crystal product, which was then converted to an alkali with aqueous ammonia to give JK-2215D01 (1.4 g, yield: 36%). $^1$H NMR (400 MHz, CDCl$_3$): δ6.84 (d, 1H), 6.78 (s, 1H), 6.52 (d, 1H), 3.97 (d, 2H), 3.56 (m, 22H), 3.41 (d, 2H), 3.34 (s, 3H), 2.83 (d, 2H), 2.75 (m, 1H), 1.84 (t, 2H), 1.47 (s, 3H), 1.53 (m, 2H), 1.28 (m, 8H).

Example 2 Preparation of Monomethoxyhexaethylene Glycol-Dezocine Conjugate (JK-2215D02)

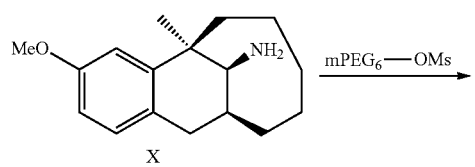

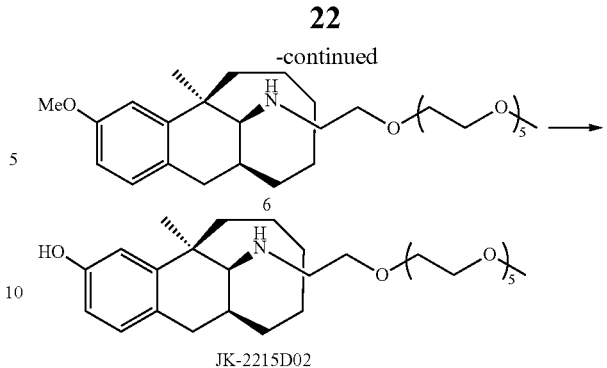

To a reaction flask, intermediate X (5.0 g, 19.3 mmol) was added, dissolved in tetrahydrofuran (100 mL), and cooled in an ice bath under a nitrogen atmosphere. Sodium hydride (1.2 g, 29.0 mmol) was added thereto. The mixture was reacted for 30 min. Then, a solution of monomethoxyhexaethylene glycol mesylate (8.7 g, 23.2 mmol) in tetrahydrofuran (50 mL) was added dropwise thereto. After the completion of the dropwise addition, the ice bath was removed. The mixture was continued to react at room temperature. After the reaction was completed, the reaction mixture was evaporated to dryness. The residue was added with water (200 mL), washed with dilute hydrochloric acid and saturated brine, dried, filtered and then concentrated. The crude product is purified by column chromatography to give a solid product (6) (7.7 g, yield 74.6%). $^1$H NMR (400 MHz, CDCl$_3$): δδ 6.85 (d, 1H), 6.78 (s, 1H), 6.51 (d, 1H), 3.84 (s, 3H), 3.56 (m, 22H), 3.34 (s, 3H), 2.83 (d, 2H), 2.75 (s, 3H), 1.84 (t, 2H), 1.55 (m, 5H), 1.29 (m, 6H).

Compound (6) (5.0 g, 9.3 mmol) was dissolved in dichloromethane (100 mL) and cooled to −20° C. under a nitrogen atmosphere. Then, a solution of boron tribromide in dichloromethane (1.0 M, 27.9 mL) was added dropwise thereto. After the completion of the dropwise addition, the system naturally rose to room temperature and allowed to react overnight. Water (100 mL) was added thereto. The mixture was stirred for 1 h, and then subjected to liquid separation. The water layer was added with aqueous ammonia, and extracted with diethyl ether (100 mL×3). The extracts were combined, washed with saturated brine, dried, filtered and then concentrated. The crude product was purified by column chromatography to give a solid product (JK-2215D02) (3.7 g, yield: 76%). $^1$H NMR (400 MHz, CDCl$_3$): δδ 6.84 (d, 1H), 6.77 (s, 1H), 6.52 (d, 1H), 3.56 (m, 22H), 3.35 (s, 3H), 2.83 (d, 2H), 2.74 (s, 3H), 1.85 (t, 2H), 1.56 (m, 5H), 1.28 (m, 6H).

Example 3 Preparation of Pentaethylene Glycol-Dezocine Conjugate (JK-2215D03)

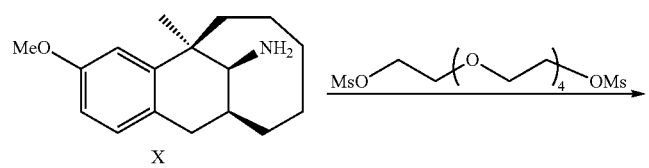

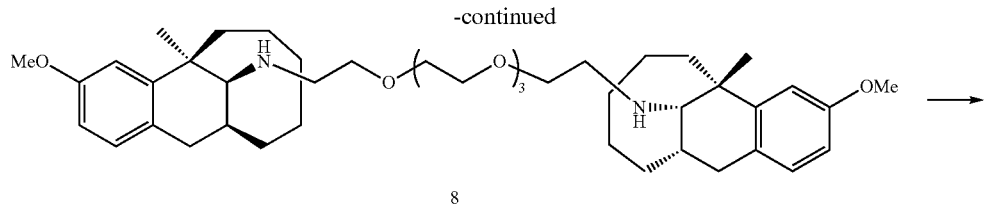

8

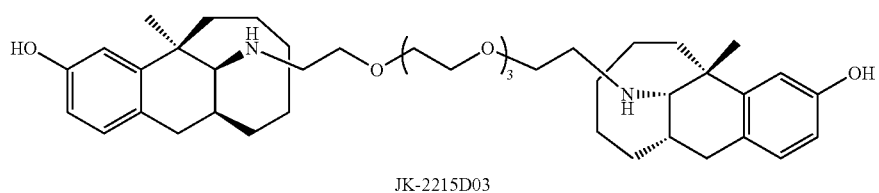

JK-2215D03

To a reaction flask, pentaethylene glycol (10.0 g, 42.0 mmol) and dichloromethane (100 mL) were added, and the resulting mixture was cooled to 0° C. with stirring. Triethylamine (17.0 g, 168.0 mmol) was added dropwise thereto. The reaction mixture was stirred for 10 minutes. Methanesulfonyl chloride (14.4 g, 126.0 mmol) was added to the reaction mixture. The mixture was reacted under stirring at room temperature. After the reaction was completed, the reaction mixture was added with distilled water, and then extracted with dichloromethane (100 mL×3). The organic layers were combined, washed with distilled water (100 mL×3), dried over anhydrous sodium sulfate, filtered and concentrated to dryness under reduced pressure to give an oily substance (7) (19.6 g, yield: 85.3%). $^1$H NMR (400 MHz, CDCl$_3$): δ3.81 (m, 4H), 3.62 (m, 4H), 3.56 (m, 12H), 3.18 (s, 6H).

To a reaction flask, intermediate X (5.0 g, 19.3 mmol) was added, dissolved in tetrahydrofuran (100 mL), and cooled in an ice bath under a nitrogen atmosphere. Sodium hydride (1.2 g, 29.0 mmol) was added thereto. The mixture was reacted for 30 min. Then, a solution of pentaethylene glycol mesylate (7) (5.3 g, 9.7 mmol) in tetrahydrofuran (100 mL) was added dropwise thereto. After the completion of the dropwise addition, the ice bath was removed. The mixture was continued to react at room temperature. After the reaction was completed, the reaction mixture was evaporated to dryness. The residue was added with water (200 mL), washed with dilute hydrochloric acid and saturated brine, dried, filtered and then concentrated. The crude product was purified by column chromatography to give a solid product (8) (4.2 g, yield: 72.4%). $^1$H NMR (400 MHz, CDCl$_3$): δδ 6.85 (d, 2H), 6.78 (s, 2H), 6.51 (d, 2H), 3.83 (s, 6H), 3.56 (m, 12H), 3.50 (d, 4H), 2.96 (m, 4H), 2.83 (m, 4H), 2.75 (d, 2H), 1.95 (m, 2H), 1.64 (m, 4H), 1.57 (s, 6H), 1.33 (m, 4H), 1.29 (m, 12H).

Compound (8) (3.7 g, 0.6 mmol) was dissolved in dichloromethane (100 mL) and cooled to −20° C. under a nitrogen atmosphere. Then, a solution of boron tribromide in dichloromethane (1.0 M, 3.6 mL) was added dropwise thereto. After the completion of the dropwise addition, the system naturally rose to room temperature and allowed to react overnight. Water (100 mL) was added thereto. The mixture was stirred for 1 h, and then subjected to liquid separation. The water layer was added with aqueous ammonia, and extracted with diethyl ether (100 mL×3). The extracts were combined, then washed with saturated brine, dried, filtered and then concentrated. The crude product was purified by column chromatography to give a solid product (JK-2215D03) (2.8 g, yield: 78.2%). $^1$H NMR (400 MHz, CDCl$_3$): δ 6.86 (d, 2H), 6.79 (s, 2H), 6.52 (d, 2H), 3.55 (m, 12H), 3.51 (d, 4H), 2.97 (m, 4H), 2.82 (m, 4H), 2.74 (d, 2H), 1.96 (m, 2H), 1.62 (m, 4H), 1.55 (s, 6H), 1.31 (m, 4H), 1.28 (m, 12H).

Example 4 Preparation of Three-Arm Polyethylene Glycol-Dezocine Conjugate (JK-2215D04)

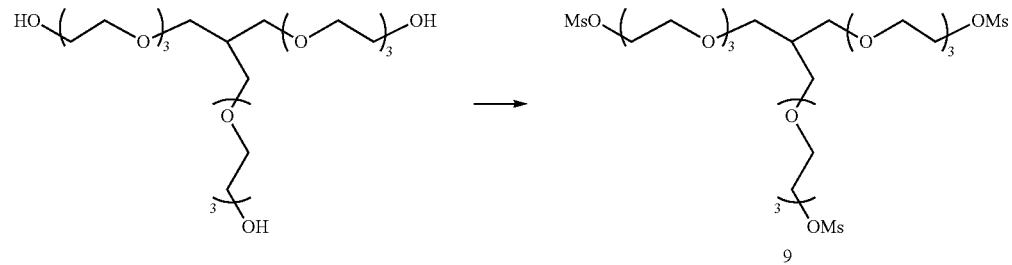

9

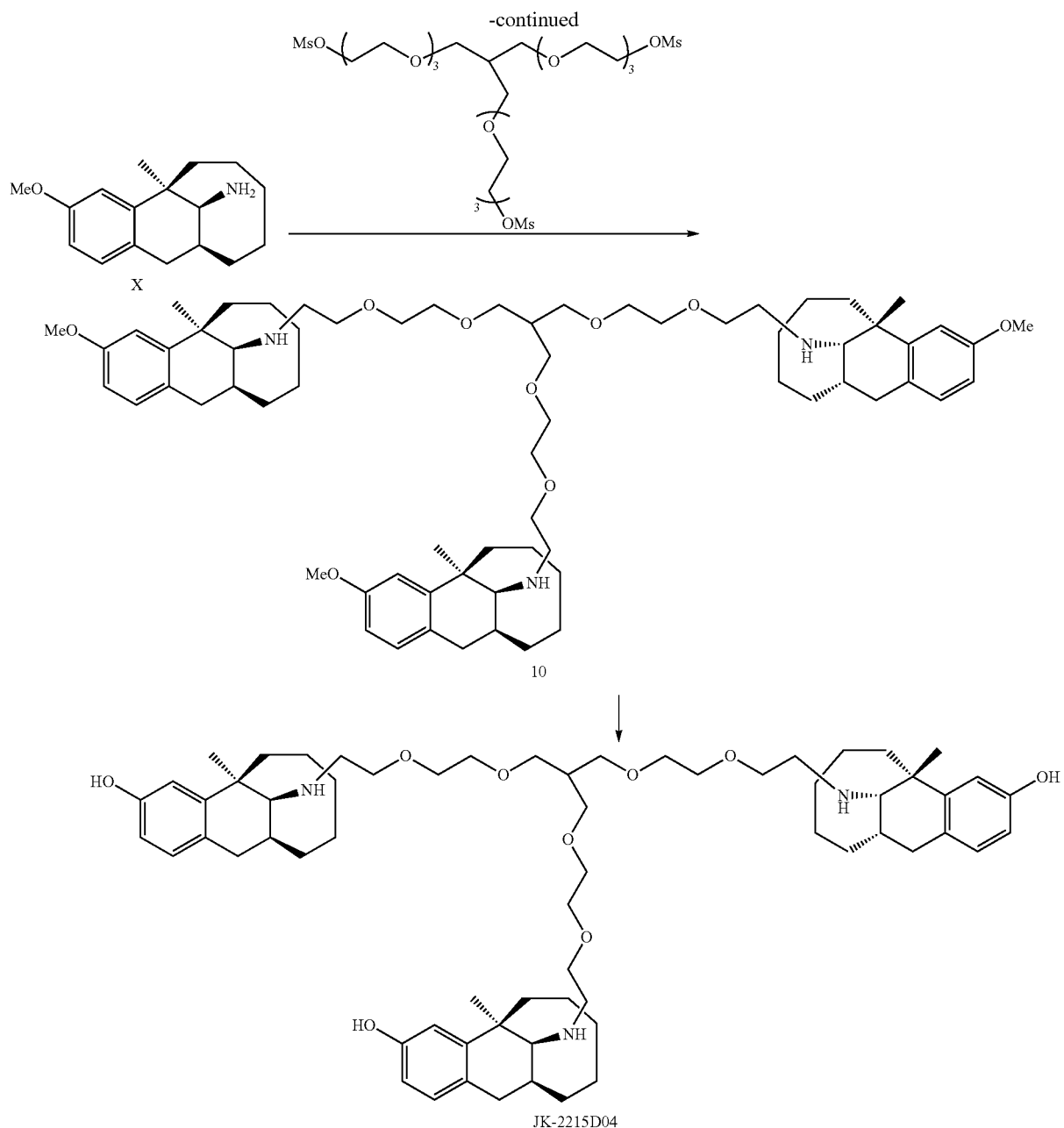

To a reaction flask, three-arm polyethylene glycol (20.0 g, 40.0 mmol) and dichloromethane (200 mL) were added, and the resulting mixture was cooled to 0° C. with stirring. Triethylamine (4.2 g, 240.0 mmol) was added dropwise thereto. The reaction mixture was stirred for 10 minutes. Methanesulfonyl chloride (20.6 g, 180.0 mmol) was added to the reaction mixture. The mixture was reacted under stirring at room temperature. After the reaction was completed, the reaction mixture was added with distilled water, and then extracted with dichloromethane (200 mL×3). The organic layers were combined, washed with distilled water (200 mL×3), dried over anhydrous sodium sulfate, filtered and concentrated to dryness under reduced pressure to give an oily substance (9) (24.5 g, yield: 83.6%). $^1$H NMR (400 MHz, CDCl$_3$): δ 3.83 (d, 18H), 3.66 (d, 18H), 3.45 (d, 6H), 3.28 (s, 9H), 2.48 (m, 1H).

To a reaction flask, intermediate X (9.3 g, 36.0 mmol) was added dissolved in tetrahydrofuran (200 mL), and cooled in an ice bath under a nitrogen atmosphere. Sodium hydride (6.5 g, 162.0 mmol) was added thereto. The mixture was reacted for 30 min. Then, a solution of three-arm polyethylene glycol mesylate (8.8 g, 12.0 mmol) in tetrahydrofuran (100 mL) was added dropwise thereto. After the completion of the dropwise addition, the ice bath was removed. The mixture was continued to react at room temperature. After the reaction was completed, the reaction mixture was evaporated to dryness. The residue was added with water (200 mL), washed with dilute hydrochloric acid and saturated brine, dried, filtered and then concentrated. The crude product was purified by column chromatography to give a solid product (10) (10.9 g, yield 74.5%). $^1$H NMR (400 MHz, CDCl$_3$): δ 6.85 (d, 3H), 6.78 (s, 3H), 6.51 (d, 3H), 3.83 (s, 9H), 3.56 (m, 12H), 3.50 (d, 6H), 3.37 (d, 6H), 2.96 (m, 6H), 2.83 (t, 6H), 2.75 (t, 3H), 2.57 (s, 1H), 1.95 (m, 3H), 1.64 (m, 6H), 1.57 (s, 9H), 1.28 (m, 24H).

Compound (10) (6.1 g, 5 mmol) was dissolved in dichloromethane (100 mL) and cooled to −20° C. under a nitrogen atmosphere. Then, a solution of boron tribromide in dichloromethane (1.0 M, 45 mL) was added dropwise thereto. After the completion of the dropwise addition, the system naturally rose to room temperature and allowed to react overnight. Water (100 mL) was added thereto. The mixture was stirred for 1 h, and then subjected to liquid separation. The water layer was added with aqueous ammonia, and extracted with diethyl ether (100 mL×3). The extracts were combined, washed with saturated brine, dried, filtered and then concentrated. The crude product was purified by column chromatography to give a solid product (JK-2215D04) (4.5 g, yield: 76.3%). $^1$H NMR (400 MHz, CDCl$_3$): δ 6.86 (d, 3H), 6.77 (s, 3H), 6.52 (d, 3H), 3.57 (m, 12H), 3.51 (d, 6H), 3.35 (d, 6H), 2.94 (m, 6H), 2.82 (t, 6H), 2.74 (t, 3H), 2.55 (s, 1H), 1.96 (m, 3H), 1.64 (m, 6H), 1.58 (s, 9H), 1.29 (m, 24H).

Example 5 Preparation of Four-Arm Polyethylene Glycol-Dezocine Conjugate (JK-2215D05)

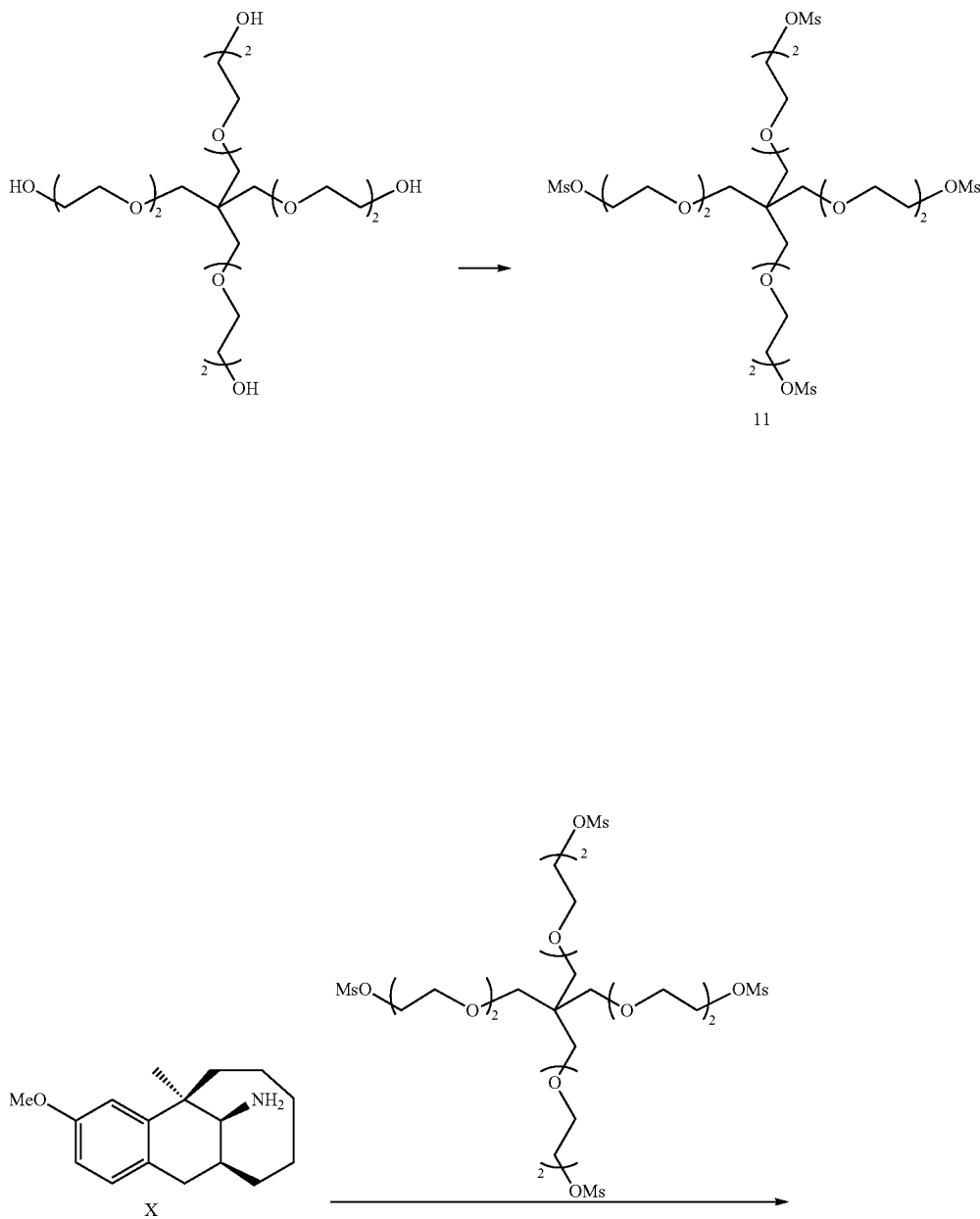

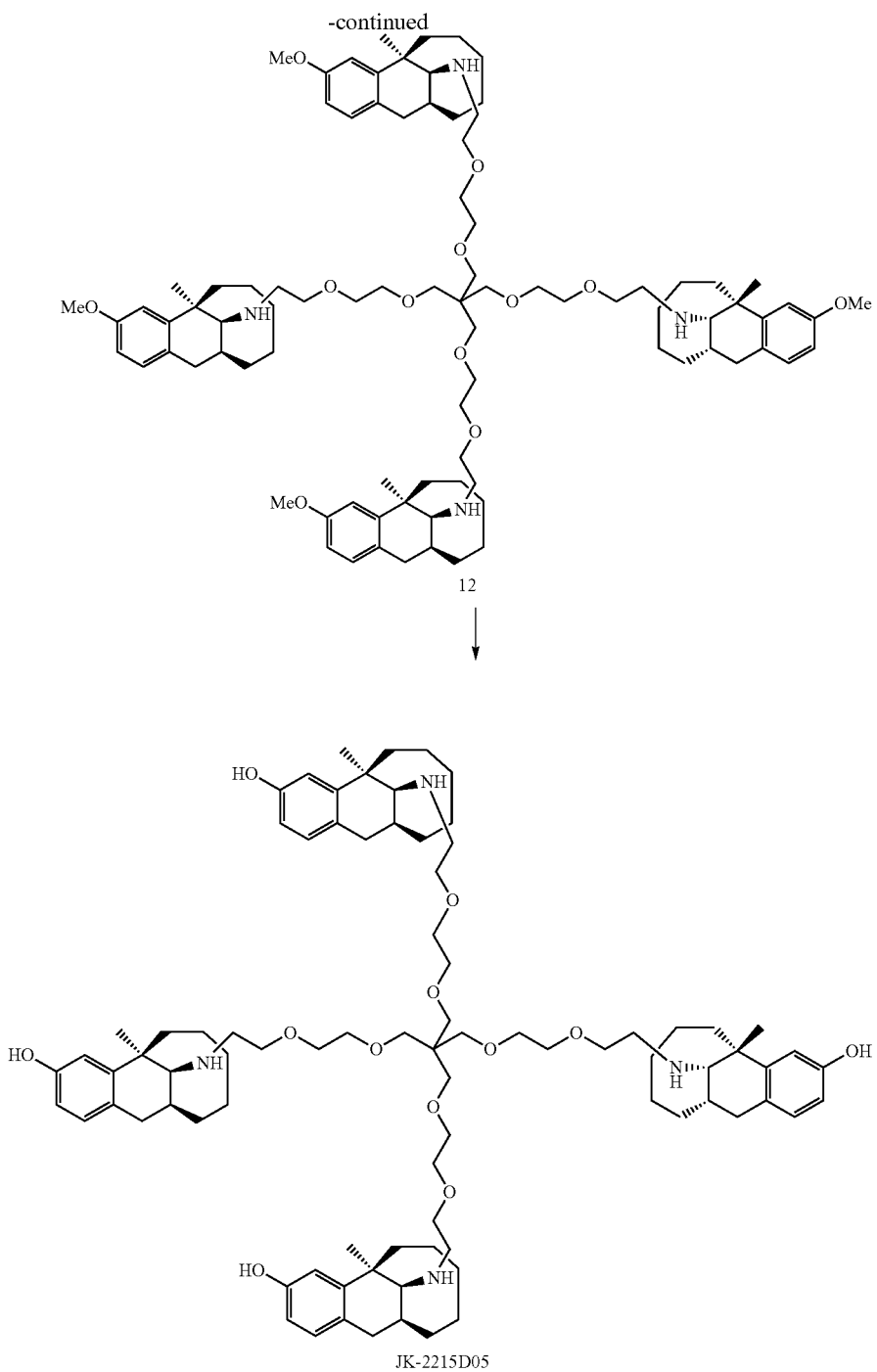

JK-2215D05

To a reaction flask, four-arm polyethylene glycol (10.0 g, 20.5 mmol) and dichloromethane (100 mL) were added, and the resulting mixture was cooled to 0° C. with stirring. Triethylamine (16.6 g, 164.0 mmol) was added dropwise thereto. The reaction mixture was stirred for 10 minutes. Methanesulfonyl chloride (14.1 g, 123.0 mmol) was added to the reaction mixture. The mixture was reacted under stirring at room temperature. After the reaction was completed, the reaction mixture was added with distilled water, and then extracted with dichloromethane (100 mL×3). The organic layers were combined, washed with distilled water (100 mL×3), dried over anhydrous sodium sulfate, filtered and concentrated to dryness under reduced pressure to give an oily substance (11) (14.1 g, yield: 86.0%). $^1$H NMR (400 MHz, CDCl$_3$): δ 3.83 (d, 24H), 3.66 (d, 24H), 3.56 (d, 8H), 3.28 (s, 12H).

To a reaction flask, intermediate X (12.4 g, 48.0 mmol) was added, dissolved in tetrahydrofuran (150 mL), and cooled in an ice bath under a nitrogen atmosphere. Sodium hydride (11.5 g, 288.0 mmol) was added thereto. The mixture was reacted for 30 min. Then, a solution of four-arm polyethylene glycol mesylate (9.6 g, 12.0 mmol) in tetrahydrofuran (100 mL) was added dropwise thereto. After the completion of the dropwise addition, the ice bath was removed. The mixture was continued to react at room temperature. After the reaction was completed, the reaction mixture was evaporated to dryness. The residue was added with water (150 mL), washed with dilute hydrochloric acid and saturated brine, dried, filtered and then concentrated. The crude product was purified by column chromatography to give a solid product (12) (12.8 g, yield 73.8%). $^1$H NMR (400 MHz, CDCl$_3$): δ 6.85 (d, 4H), 6.78 (s, 4H), 6.51 (d, 4H), 3.83 (s, 12H), 3.56 (m, 16H), 3.50 (d, 8H), 3.37 (d, 8H), 2.96 (m, 8H), 2.83 (d, 8H), 2.75 (t, 4H), 1.95 (m, 4H), 1.64 (m, 8H), 1.57 (s, 12H), 1.50 (m, 4H), 1.28 (in, 32H).

Compound (12) (7.3 g, 5 mmol) was dissolved in dichloromethane (100 mL) and cooled to −20° C. under a nitrogen atmosphere. Then, a solution of boron tribromide in dichloromethane (1.0 M, 60 mL) was added dropwise thereto. After the completion of the dropwise addition, the system naturally rose to room temperature and allowed to react overnight. Water (100 mL) was added thereto. The mixture was stirred for 1 h, and then subjected to liquid separation. The water layer was added with aqueous ammonia, and extracted with diethyl ether (100 mL×3). The extracts were combined, washed with saturated brine, dried, filtered and then concentrated. The crude product was purified by column chromatography to give a solid product (JK-2215D05) (5.9 g, yield: 85.1%). $^1$H NMR (400 MHz, CDCl$_3$): δ 6.86 (d, 4H), 6.77 (s, 4H), 6.52 (d, 4H), 3.55 (m, 16H), 3.51 (d, 8H), 3.34 (d, 8H), 2.95 (m, 8H), 2.84 (d, 8H), 2.76 (t, 4H), 1.95 (m, 4H), 1.65 (m, 8H), 1.56 (s, 12H), 1.51 (m, 4H), 1.29 (m, 32H).

Example 6 Pharmacokinetic Experiment (Drug Concentration in Plasma and Brain Tissue of SD Rats after Oral Administration)

Experimental Method:

Healthy SD rats, male, 6-8 weeks old, weighting 230-260 grains were used. The animals were randomly divided into 5 groups, and were orally administered with JK-2215D00 (dezocine) and tested products JK-2215D01, JK-2215D02, JK-2215D03, JK-2215D04, and JK-2215D05 at a dose of 10 mg/kg. Blood and brain tissues were collected from 3 animals at each time point before the administration (0 h) and at 0.25, 0.5, 1, 2, 4, 8, and 24 h after the administration. Approximately 300 µL blood was collected from each animal through the orbit and collected in a heparin sodium anticoagulation tube. Plasma was separated by centrifugation (2000 g, 5 minutes) within 15 minutes after blood collection. After blood collection, animals were sacrificed, and brain tissues were collected according to SOP. The collected brain tissue was immediately rinsed with ice PBS (without Ca$^{2+}$ and Mg$^{2+}$) and weighed. Subsequently, PBS was added to the tissue in a volume ratio of tissue weight to PBS buffer (without Ca$^{2+}$ and Mg$^{2+}$) of 1:4, and homogenized, and the supernatant was taken for analysis. The drug concentrations in the above plasma and brain tissue samples were determined by LC-MS/MS method Experimental Results:

The experimental results are shown in Table 1. The pharmacokinetic characteristics of each tested product after oral administration are significantly different from that of dezocine (JK-2215D00), mainly manifested in that oral absorption was significantly enhanced, plasma AUC values were about 4-6 times that of dezocine, and plasma half-life was prolonged to varying degrees. Another significant difference is brain permeability. Compared with dezocine, the brain permeability of all tested products was reduced to some extent, which showed that AUC$_{last}$ Ratio (brain/plasma) value was decreased. However, at the same time, the retention time of each sample in the brain was significantly prolonged, the elimination half-life time in the brain was about 8-10 times that of dezocine, and the AUC value in the brain was correspondingly higher than that of the same dose of dezocine.

TABLE 1

Pharmacokinetic parameters of dezocine and its PEG derivatives in blood and brain after oral administration in SD rats

| Plasma | n | $t_{1/2}$ (h) | $t_{max}$ (h) | $C_{max}$ (ng/mL) | AUC$_{last}$ (h * ng/mL) |
|---|---|---|---|---|---|
| JK-2215D00 | 3 | 1.41 | 1 | 193 | 232 |
| JK-2215D01 | 3 | 4.33 | 3 | 345 | 1366 |
| JK-2215D02 | 3 | 4.45 | 3 | 339 | 1312 |
| JK-2215D03 | 3 | 4.12 | 2 | 344 | 1233 |
| JK-2215D04 | 3 | 3.85 | 2 | 373 | 1249 |
| JK-2215D05 | 3 | 3.20 | 2 | 381 | 1061 |

| Brain | n | $t_{1/2}$ (h) | $t_{max}$ (h) | $C_{max}$ (ng/g) | AUC$_{last}$ (h * ng/g) | AUC$_{last}$ Ratio (Plasma/Brain) |
|---|---|---|---|---|---|---|
| JK-2215D00 | 3 | 2.05 | 1 | 221 | 267 | 1.149 |
| JK-2215D01 | 3 | 17.6 | 8 | 147 | 925 | 0.734 |
| JK-2215D02 | 3 | 18.7 | 8 | 166 | 993 | 0.757 |
| JK-2215D03 | 3 | 19.7 | 7 | 129 | 813 | 0.659 |
| JK-2215D04 | 3 | 21.2 | 6 | 143 | 970 | 0.777 |
| JK-2215D05 | 3 | 17.3 | 6 | 156 | 863 | 0.813 |

Example 7 Pharmacodynamic Experiment (Effect of Dezocine and its PEG Derivatives on CFA Rat Model)

Experimental Method:

Healthy SD rats, male, 6-8 weeks old, weighing 230-260 grains were used. After 7 days of adaptive feeding, CFA inducer was injected subcutaneously to the planta of the left rear feet, 50 µL per animal (M. Tuberculosis, H37 RA at a concentration of 4 mg/mL) Three days after the injection, the basal value of Frey's hair pain threshold was determined, and the animals were randomly divided into 6 groups based on the basal values. The dosage regimen is shown in Table 2. The Frey's hair pain threshold for each animal at 0.25, 2, 6 and 24 h after administration was determined, and the test was repeated 2-3 times, and the mean value was taken as the final pain threshold of the animal stimulated by Frey's hair. The experimental results were expressed as "mean±standard deviation". The data of each group were statistically analyzed by SPSS 17.0 software package. Statistical method One-Way ANOVA was used to compare whether there was any statistical difference between the drug administration groups and the solvent group. P<0.05 indicated statistical significance.

TABLE 2

Grouping and administration of experimental animals

| Group | Drug | Dosage (mg/kg) | Route of administration | Number of animals |
|---|---|---|---|---|
| 1 | Solvent | — | oral | 8 |
| 2 | JK-2215D00 | 10 | oral | 8 |
| 3 | JK-2215D01 | 10 | oral | 8 |

TABLE 2-continued

Grouping and administration of experimental animals

| Group | Drug | Dosage (mg/kg) | Route of administration | Number of animals |
|---|---|---|---|---|
| 4 | JK-2215D02 | 10 | oral | 8 |
| 5 | JK-2215D03 | 10 | oral | 8 |
| 6 | JK-2215D04 | 10 | oral | 8 |
| 7 | JK-2215D05 | 10 | oral | 8 |

Experimental Results:

The experimental results are shown in Table 3. Both dezocine and its PEG derivatives had an analgesic effect to some extent after oral administration. Overall, the PEG derivatives on the N atom had an analgesic activity significantly stronger than that of dezocine at the same dose, moreover, the duration of analgesic effect was also significantly longer than that of dezocine. Each sample still had significant analgesic activity at 24 h after administration, while the analgesic effect of dezocine at 6 h after administration was not significant, which may be related to the longer retention time of each sample in the brain.

Compared with dezocine, the conjugates with polyethylene glycol at the N atom of dezocine have larger molecular weight, thus have smaller administration amount of dezocine at the same administration dosage (10 mg/kg), but at the same time, they can provide a more diverse mode of administration, such as oral administration, and have better drug absorption, stronger analgesic effect and longer analgesic duration.

TABLE 3

Pain threshold value of each group of animals stimulated by Frey's hair (mean ± standard deviation)

| Group | Frey's hair (g) | | | | |
|---|---|---|---|---|---|
| | 0 h | 0.25 h | 2 h | 6 h | 24 h |
| Solvent | 7.9 ± 1.0 | 7 ± 1.0 | 8.2 ± 0.7 | 8.2 ± 1.3 | 7.4 ± 1.6 |
| JK-2215D00 | 7.7 ± 1.1 | 9.8 ± 1.0** | 10.2 ± 2.7* | 9.2 ± 1.4* | 7.5 ± 1.8 |
| JK-2215D01 | 7.6 ± 0.8 | 8.7 ± 1.3** | 9.1 ± 1.3** | 8.7 ± 1.1** | 7.8 ± 1.4* |
| JK-2215D02 | 7.8 ± 0.8 | 10.3 ± 1.2** | 12.1 ± 1.5** | 13.2 ± 0.9** | 10.7 ± 1.5* |
| JK-2215D03 | 7.7 ± 1.4 | 9.2 ± 1.4** | 11.2 ± 2.0* | 11.4 ± 0.9** | 10.6 ± 2.0* |
| JK-2215D04 | 7.7 ± 1.1 | 8.8 ± 0.9* | 10.3 ± 1.9* | 11.1 ± 0.9** | 9.8 ± 1.9* |
| JK-2215D05 | 7.7 ± 1.3 | 10.7 ± 1.3** | 11.7 ± 1.2** | 12.9 ± 1.9** | 10.9 ± 1.2** |

Note:
*P < 0.05,
**P < 0.01 compared with the solvent control group.

The above are only the preferred embodiments of the invention, and are not intended to limit the invention. Any modifications, equivalent substitutions, etc., made within the spirit and scope of the invention are intended to be included within the scope of the invention.

The invention claimed is:

1. A conjugate of dezocine and polyethylene glycol having the following structure:

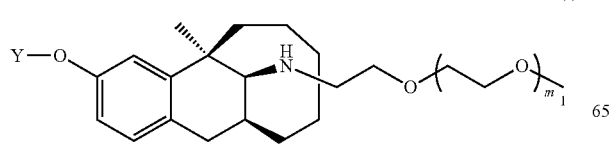

(I)

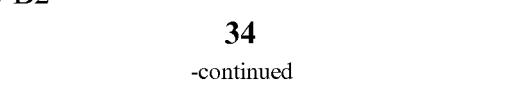

(II)

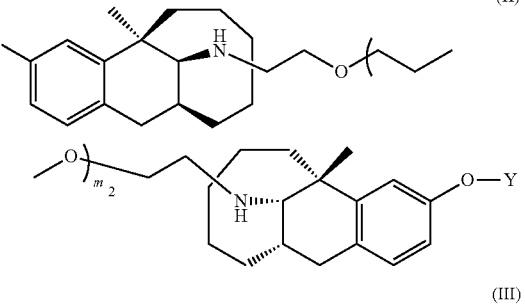

(III)

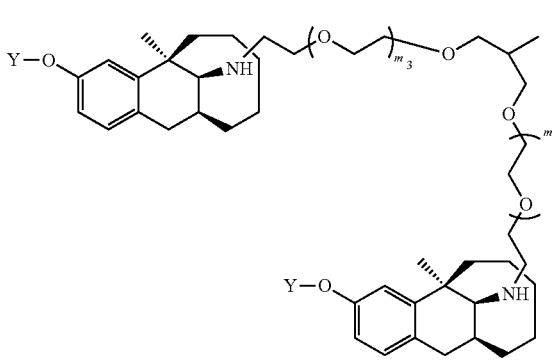

-continued

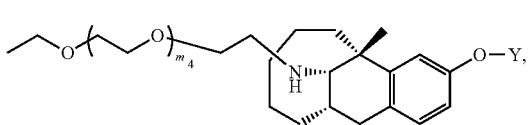

or

-continued (IV)

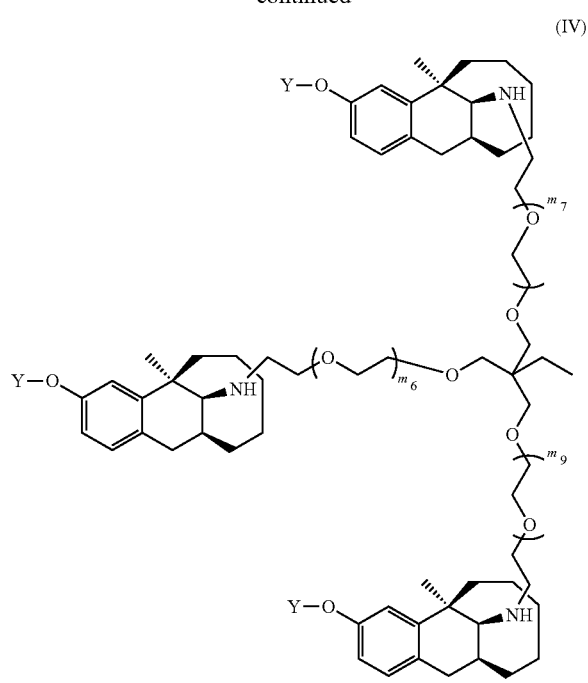

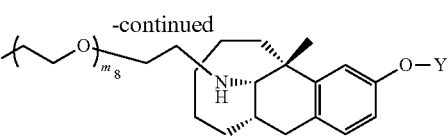

wherein, Y is selected from: H or a protecting group; and $m_1$, $m_2$, $m_3$, $m_4$, $m_5$, $m_6$, $m_7$, $m_8$ and $m_9$ are independently selected from integers of 0-20.

2. The conjugate of claim 1, wherein the Y is H.

3. The conjugate of claim 1, wherein the protecting group is —$CH_3$.

4. The conjugate of claim 1, wherein $m_1$, $m_2$, $m_3$, $m_4$, $m_5$, $m_6$, $m_7$, $m_8$ and $m_9$ are independently selected from integers of 1-10.

5. The conjugate of claim 1, wherein $m_1$ is an integer of 2-8, $m_2$ is an integer of 2-8, $m_3$, $m_4$ and $m_5$ are independently selected from integers of 1-6, and $m_6$, $m_7$, $m_8$ and $m_9$ are independently selected from integers of 0-6.

6. The conjugate of claim 1, wherein $m_1$ is an integer of 4-6, $m_2$ is an integer of 2-5, $m_3$, $m_4$ and $m_5$ are independently selected from integers of 2-5, and $m_6$, $m_7$, $m_8$ and $m_9$ are independently selected from integers of 1-5.

7. The conjugate of claim 1, wherein $m_1$ is 5, $m_2$ is 3, $m_3$, $m_4$ and $m_5$ are 2, and $m_6$, $m_7$, $m_8$ and $m_9$ are 1.

8. The conjugate of claim 1 having the following structure:

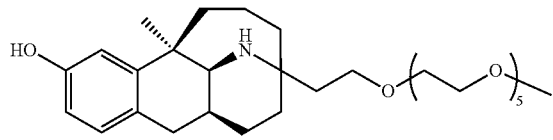

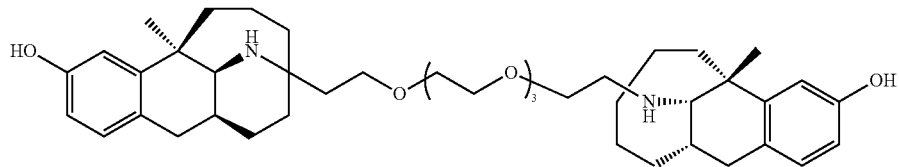

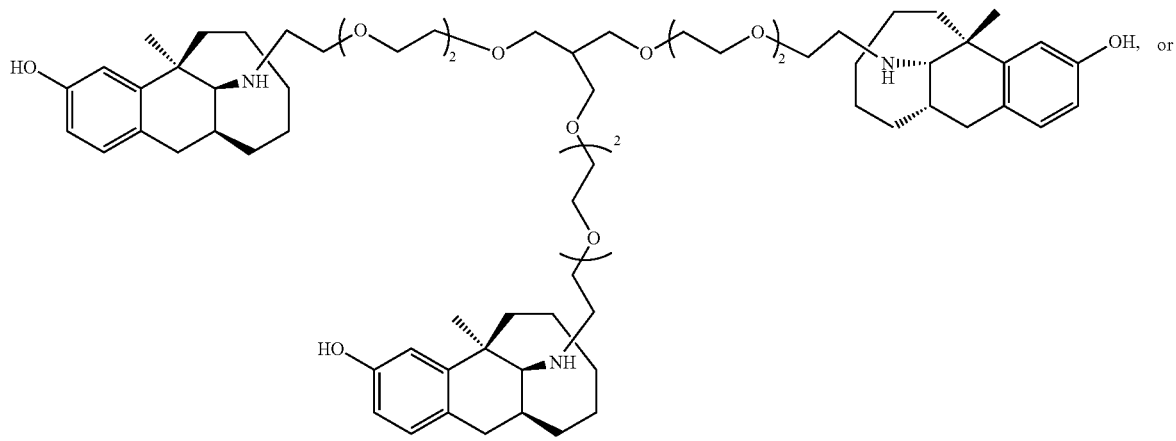

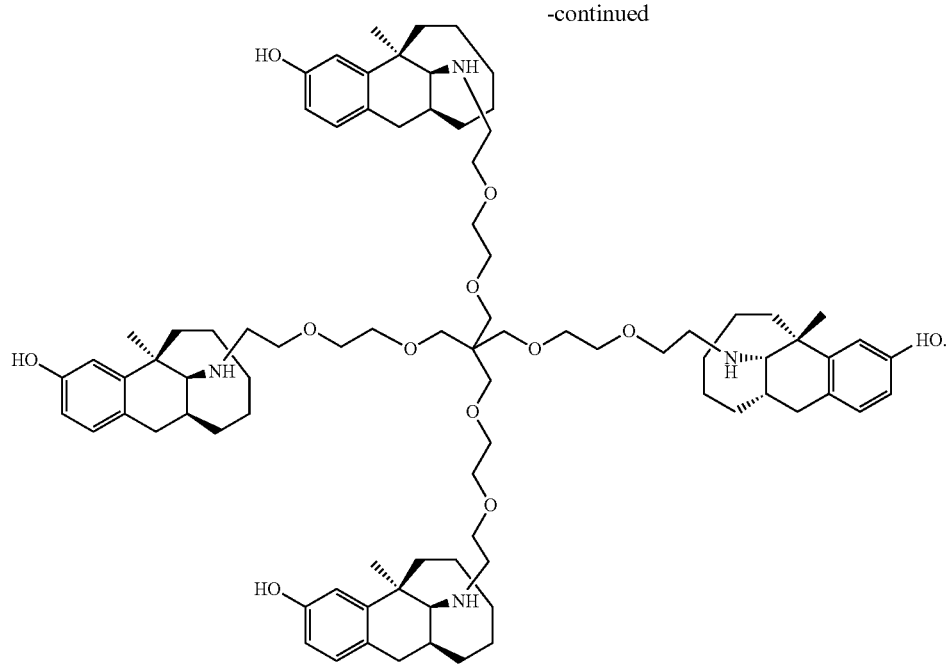

9. A preparation method of the conjugate of claim 1, comprising the following specific steps: modifying a terminal group of polyethylene glycol with a leaving group, and then subjecting the polyethylene glycol to a nucleophilic substitution reaction with dezocine or an intermediate or a derivative thereof to obtain the conjugate.

10. The preparation method of claim 9 further comprising a step of deprotecting: dissolving the conjugate of dezocine and polyethylene glycol, adding a deprotecting reagent, reacting, and then separating and purifying the product.

11. A pharmaceutical composition comprising the conjugate of claim 1 and a pharmaceutically acceptable carrier or excipient.

12. The pharmaceutical composition of claim 11, wherein, in the conjugate, the Y is H.

13. The pharmaceutical composition of claim 12, wherein, in the conjugate, $m_1$, $m_2$, $m_3$, $m_4$, $m_5$, $m_6$, $m_7$, $m_8$ and $m_9$ are independently selected from integers of 1-10.

14. The pharmaceutical composition of claim 12, wherein, in the conjugate, $m_1$ is an integer of 2-8, $m_2$ is an integer of 2-8, $m_3$, $m_4$ and $m_5$ are independently selected from integers of 1-6, and $m_6$, $m_7$, $m_8$ and $m_9$ are independently selected from integers of 0-6.

15. The pharmaceutical composition of claim 12, wherein the conjugate has the following structure:

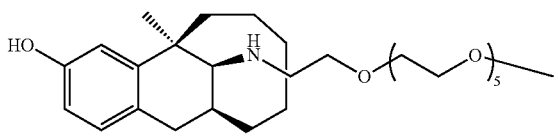

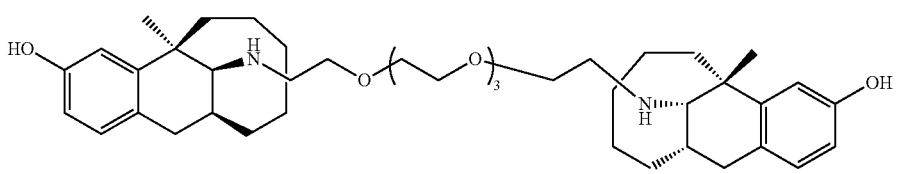

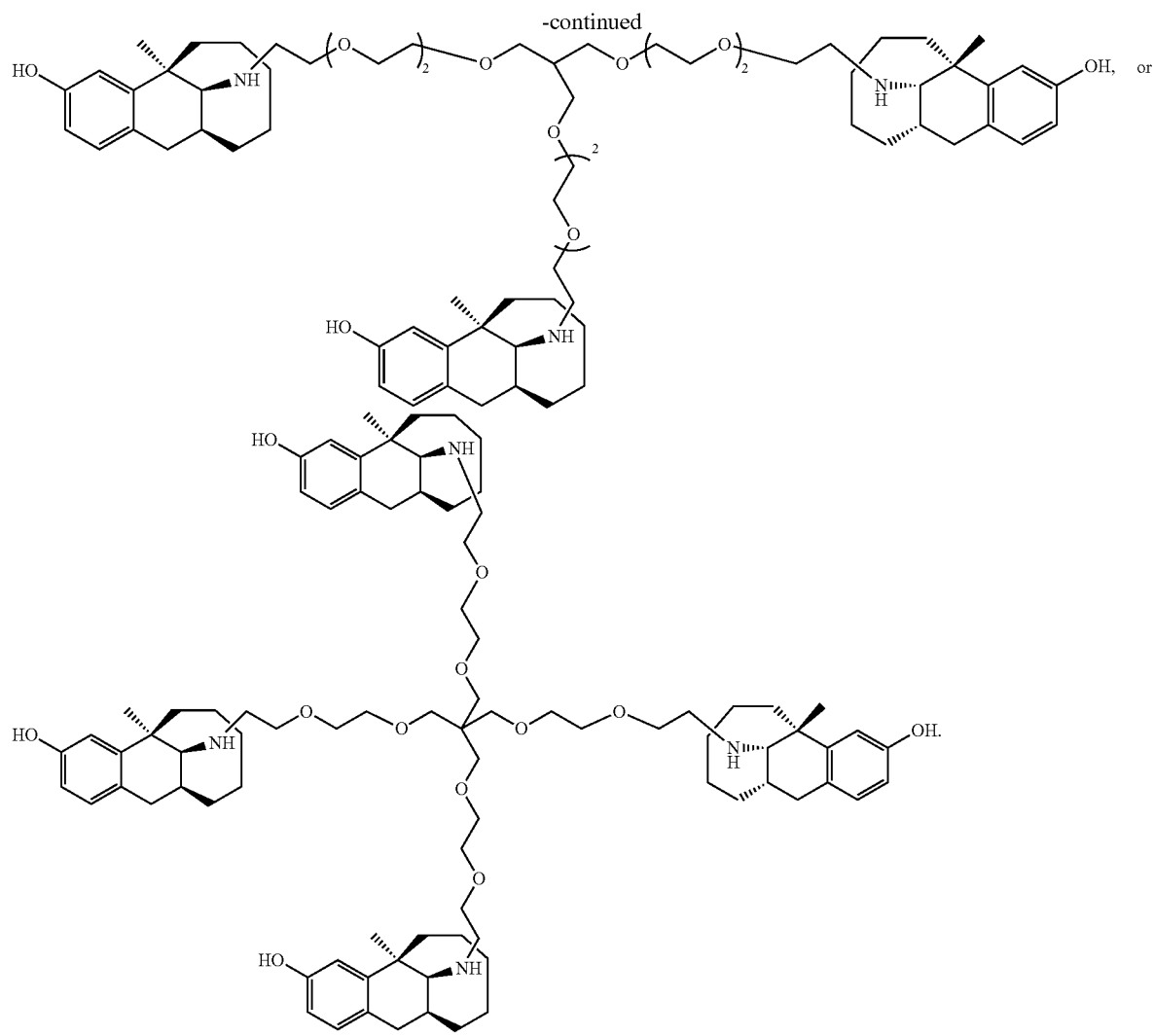

16. An analgesic method comprising a step of administering an effective amount of the pharmaceutical composition of claim 11 to a subject in such need.

17. The method of claim 16, wherein, in the conjugate, the Y is H.

18. The method of claim 17, wherein, in the conjugate, $m_1$, $m_2$, $m_3$, $m_4$, $m_5$, $m_6$, $m_7$, $m_8$ and $m_9$ are independently selected from integers of 1-10.

19. The method of claim 17, wherein, in the conjugate, $m_1$ is an integer of 2-8, $m_2$ is an integer of 2-8, $m_3$, $m_4$ and $m_5$ are independently selected from integers of 1-6, and $m_6$, $m_7$, $m_8$ and $m_9$ are independently selected from integers of 0-6.

20. The method of claim 17, wherein, wherein the conjugate has the following structure:

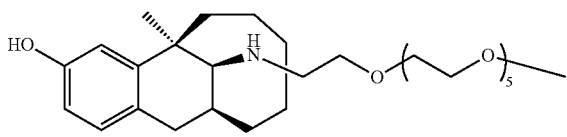

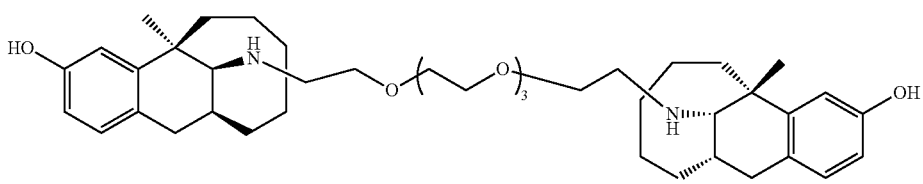

41
42
-continued
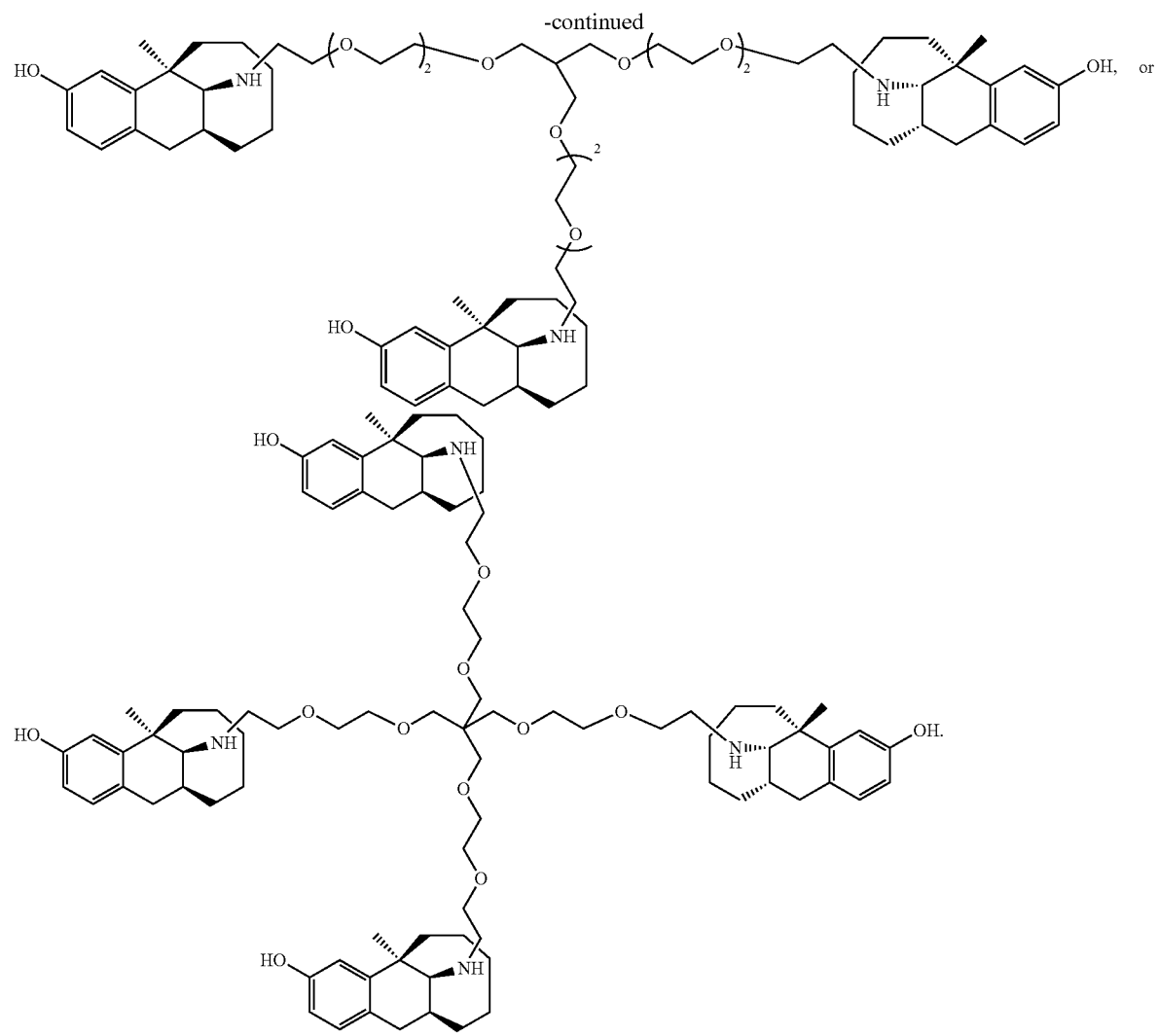
* * * * *